US007708991B2

(12) United States Patent
Cole

(10) Patent No.: US 7,708,991 B2
(45) Date of Patent: May 4, 2010

(54) METHOD FOR TREATING CANCER AND IDENTIFYING NOVEL ANTI-CANCER COMPOUNDS

(75) Inventor: Laurence A Cole, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 680 days.

(21) Appl. No.: 11/058,542

(22) Filed: Feb. 15, 2005

(65) Prior Publication Data

US 2005/0260196 A1 Nov. 24, 2005

Related U.S. Application Data

(60) Provisional application No. 60/545,102, filed on Feb. 17, 2004, provisional application No. 60/577,683, filed on Jul. 6, 2004.

(51) Int. Cl.
*A61K 39/395* (2006.01)
(52) U.S. Cl. .................. 424/130.1; 424/141.1
(58) Field of Classification Search ........................ None
See application file for complete search history.

(56) References Cited

OTHER PUBLICATIONS

Busken, C et al, (Digestive Disease Week Abstracts and Itinerary Planner, 2003, abstract No:850).*
Cole et al. (2006, J. Reprod. Med. 51(11):919-29) (abstract only).*
Lei et al. (1999, Trophoblast Research 13:147-159).*
Cole et al. (2007, Molecular and Cellular Endocrinology 260-262:228-236).*
Birken et al. (1999, Endocrine 10(2):137-44).*
Sandhu (1992, Crit. Rev. Biotechnol. 12(5-6):437-62; abstract only).*
Free Online Medical Dictionary (http://medical-dictionary. thefreedictionary.com/eutopic as downloaded on May 6, 2007).*
Bagshawe et al, Br J Cancer, 1988, 58:700-703.*
Birken, S et al. "Development and Characterization of Antibodies to a Nicked and Hyperglycosylated Form of hCG from a Choriocarcinoma Patient" Endocrine. Apr. 1999, vol. 10, No. 2, pp. 137-144.
Cole, LA et al. "Hyperglycosylated Human Chorionic Gonadotropin (invasive Trophoblast Antigen) Immunoassay. A new Basis for Gestational Down Syndrome Screening." Clinical Chemistry. 1999 vol. 45, No. 12, pp. 2109-2119.
Cole LA, Clin. Chem. 1997;43:2233-443.
Cole LA, Kardana, A, Clin Chem. 1992;38:263-70.
Cole LA, Hussa RO, Adv. Exp. Med. Biol. 1984;176:245-70.
Cole, LA, Trophoblast Research 1987;2:139-48.
Cole LA, J. Clin. Endocrinol. Metab. 1987;65:811-13.
Amano J et al., J. Biol. Chem. 1988;263:1157-65.
Elliott MM et al., Endocrine 1997;7:15-32.
Takamatsu S, et al., Cancer Res 1999;59:3949-53.
Kobata A, Takeuchi M., Biochim. Biophys. Acta. 1999;1455:315-26.
Peters BP et al., J. Biol. Chem. 1984;259:15123-30.
Hussa RO, J. Clin. Endocrinol. Metab. 1977;44:1154-62.
Mann K, Karl HJ, Cancer 1983;52:654-60.
Imamura S et al., Clin. Chim. Acta 1987;163:339-49.
Cole LA et al., Clin. Chem. 1999;45:2109-19.
Cole LA et al., Clin. Biochem. 2003;36:647-655.
Birken S, et al., Endocrine 1999;10:137-44.
O'Connor JF, et al., Prenat. Diagn. 1998;18:1232-40.
Kovalesvskaya G et al., J. Endocrinol. 2002; 172:497-506.
Kovalesvskaya G, et al., J. Endocrinol. 1999;161:99-106.
Kovaleskaya G et al., Mol. Cell. Endocrinol. 2002;94:147-55.
Butler SA, et al., Clin. Chem. 2001;47:2131-06.
Cole LA et al., Am. J. Obstet. Gynecol. 2004;190:100-05.
Genbacev O. et al., Human Reproduction 1999;2-59-66.
Tarrade A, et al., Biology of Reproduction 2002; 67:1628-37.
Lei ZM, et al., Troph. Res. 1999;13:147-59.
Lapthom AJ et al., Nature 369:455-461, 1994.
Wu H, et al., Structure 1994;2:545-8.
Lala PK et al., Cancer Metast. Rev. 9:369-379, 1990.
Strickland S, Richards, WG, Cell 71:355-357, 1992.
Lash GE, et al, Placenta 20:661-7, 1999.
Caniggia L. et al., J. Clin. Invest. 103:1641-50, 1999.
Khoo NK, et al., Intl. J. Cancer 77:429-39, 1998.
Graham CH, et al., Biol. Reprod. 46:561-72, 1992.
Lala PK, Hamilton GS, Placenta 17:545-55, 1996.
Mitchell EJ, et al., Mol. Biol. Cell 3:1295-307, 1992.
Chen J, et al., Toxicology 186:21-31, 2003.
Makrigiannakis A et al., Biochemical Pharmacol. 65:917-21, 2003.
Aschkenazi S et al., Biol. Reprod. 66:1853-61,2002.
Leach RE et al., Lancet 360:1215-9,2002.
Kauma S, et al., American Journal of Obstetrics and Gynaecology 163:1430-7, 1990.
Kayisli UA et al., Am. J. Reprod. Immunol. 47:213-21,2002.
Hung TH, et al., Circulation Res. 90:1274-81, 2002.
Zhou Y et al., Am. J. Path. 160:1405-23,2002.
Emmer PM, et al., Human Reprod. 17:1072-80, 2002.
Selam B, et al., Biol Reprod. 65:979-85, 2001.
Mor G, et al., Am. J. Reprod. Immunol. 40:89-94,1998.
Simpson H, et al., Placenta, 23:44-58,2002.
Lysiak JJ, et al., Placenta 16:221-31, 1995.
Selick CE, et al., J. Clin. Endocr. Metab. 1994:78:592-6.
Vuckovic M, et al. Pathobiology 60:149-51,1992.
Fei G, et al., Contraception 64:193-200,2001.
Neale D. et al., J. Matern Fetal Neonat Med. 13:39-44, 2003.
Aschkenazi S. et al., Biol. Reprod. 66:1853-61, 2002.
Kamsteeg M., et al., Oncogene 22:2611-20, 2003.
Mor G, et al., Biochem. Pharmacol. 64:1305-15,2002.
Song J, et al., Molec. Human Reprod. 8:447-55, 2002.
Xu G, et al., Biochem. Biophys. Res. Commun. 294:1079-86, 2002.
Graham CH, et al., Exper. Cell Res. 214:93-9, 1994.
Butler SA, et al., Ann. Clin. Biochem 35:754-60, 1998.
Dai D, et al., Mol. Cancer Ther. 4:169-75,2005.

* cited by examiner

*Primary Examiner*—Misook Yu
*Assistant Examiner*—Mark Halvorson
(74) *Attorney, Agent, or Firm*—Henry D. Coleman; R. Neil Sudol; William J. Sapone

(57) ABSTRACT

The present invention relates to compositions and methods for treating cancer, especially epithelial and eutopic cancers using inhibitors of H-HCG or β-H-HCG, as well as vaccines for use in oncostasis or reducing the likelihood of recurrence of cancer after remission. In addition, the present invention provides a method for reducing the likelihood that a woman will become pregnant or that an unwanted pregnancy may be terminated.

12 Claims, 14 Drawing Sheets

Figure 1

α-Subunit ala-pro-asp-val-gln-asp-cys-pro-glu-cys-thr-leu-gln-glu-asp-pro-phe-phe-ser-gln-pro-gly-
1 ↑ 2 ↑ 3 ↑ 4
ala-pro-ile-leu- gln-cys-met-gly-cys-cys-phe-ser-arg-ala-tyr-pro-thr-pro-leu-arg-ser-lys-
23                N                                                      42↑43
lys-thr-met-leu-val-gln-lys-asn-val-thr-ser-glu-ser-thr-cys-cys-val-ala-lys-ser-tyr-asn-arg-
45                          N
val-thr-val-met-gly-gly-phe-lys-val-glu-asn-his-thr-ala-cys-his-cys-ser-thr-cys-tyr-tyr-his-
68                                  78
lys-ser
  92

β-subunit of hCG

N
ser-lys-glu-pro-leu-arg-pro-arg-cys-arg-pro-ile-asn-ala-thr-leu-ala-val-glu-lys-glu-gly-
1                   N           13
cys-pro-val-cys-ile-thr-val-asn-thr-thr-ile-cys-ala-gly-tyr-cis-pro-thr-met-thr-arg-val-
23                                                                      43↑ 44↑
leu-gln-gly-val-leu-pro-ala-leu-pro-gln-val-val-cys-asn-tyr-arg-asp-val-arg-phe-glu-
45↑       47↑48
ser-ile-arg-leu-pro-gly-cys-pro-arg-gly-val-asn-pro-val-val-ser-tyr-ala-val-ala-leu-ser-
66                            75↑ 76
cys-gln-cys-ala-leu-cys-arg-arg-ser-thr-thr-asp-cys-gly-gly-pro-lys-asp-his-pro-leu-thr-
88                                              O                  O
cys-asp-asp-pro-arg-phe-gln-asp-ser-ser-ser-ser-lys-ala-pro-pro-pro-ser-leu-pro-ser-
110 O                O                      121                127
pro-ser-arg-leu-pro-gly-pro-ser-asp-thr-pro-ile-leu-pro-gln
131 132             138                          145

FIGURE 2

Table 1

| Source | Total hCG mean ± SD (see source) | Hyperglycosylated hCG, mean ± SD (see source | Proportion Hyperglycosylated hCG, Mean ± SD |
|---|---|---|---|
| SERUM, ng/ml | | | |
| a) Trophoblast disease and cancer | | | |
| After evacuation of partial mole, n=14 cases | 1407 ± 2455 | 18 ± 33 | 2 ± 1% [a] |
| After evacuation of complete mole, n=129 cases | 15997 ± 31263 | 1131 ± 2573 | 6 ± 6% [a] |
| Choriocarcinoma, n=17 cases | 35965 ± 47788 | 36323 ± 52688 | 83 ± 41% [a] |
| Testicular germ cell malignancy, n=4 cases | 758 ± 1266 | 658 ± 1041 | 90 ± 35% [a] |
| b) Pregnancy | | | |
| 3rd complete week of pregnancy, n=13 cases | 34 ± 39 | 12 ± 12 | 50 ± 24% [b] |
| 4th complete week of pregnancy, n=29 cases | 89 ± 124 | 28 ± 24 | 43 ± 15% |
| 5th complete week of pregnancy, n=17 cases | 354 ± 575 | 71 ± 81 | 31 ± 10% |
| 6th complete week of pregnancy, n=9 cases | 2220 ± 3784 | 201 ± 290 | 23 ± 15% [b] |
| URINE ng/mg creatinine | | | |
| a) Trophoblast disease and cancer | | | |
| Quiescent gestation trophoblastic disease, 53 cases | 75 ± 125 | 1 ± 6 | 0.8 ± 0.3% [a] |
| Choriocarcinoma, 20 cases | 19642 ± 34856 | 18030 ± 35404 | 84 ± 24% [a] |
| b) Pregnancy | | | |
| 4th complete week of pregnancy, n=60 cases | 105 ± 159 | 84 ± 161 | 72 ± 95% [b] |
| 5th complete week of pregnancy, n=78 cases | 373 ± 610 | 180 ± 276 | 54 ± 31% |
| 6th complete week of pregnancy, n=15 cases | 537 ± 645 | 122 ± 181 | 23 ± 13% |
| 7th complete week of pregnancy, n=6 cases | 1688 ± 1964 | 174 ± 259 | 9 ± 6% [b] |
| 8-11th complete week of pregnancy, n=46 cases | 2474 ± 2058 | 165 ± 250 | 7 ± 11% |
| 12-15th complete week of pregnancy, n=150 case | 1158 ± 1236 | 74 ± 49 | 11 ± 23% |
| 16-19th complete week of pregnancy, n=125 cases | 731 ± 638 | 27 ± 26 | 6 ± 6% |
| 20-23rd complete week of pregnancy, n=26 cases | 402 ± 336 | 8 ± 9 | 3 ± 5% |
| 24-42nd complete week of pregnancy, n=98 cases | 813 ± 1647 | 13 ± 20 | 3 ± 4% [b] |

Figure 3

Table 2

| Sample code | Oligosaccharide composition | Biological activity |
|---|---|---|
| P7 Individual pregnancy hCG | 22%, 18%, 19% | 0.43 |
| P8 Individual pregnancy hCG | 17%, 22%, 13% | 0.55 |
| P9 Individual pregnancy hCG | 9%, 17%, 15% | 0.66 |
| Mean ± standard deviation | | 0.55 ± 0.16 [a] |
| | | |
| C3 Individual choriocarcinoma hCG | 24%, 48%, 88% | 0.14 |
| C5 Individual choriocarcinoma hCG | 20%, 48%, 100% | 0.25 |
| C7 Individual choriocarcinoma hCG | 37%, 57%, 68% | 0.39 |
| Mean ± standard deviation | | 0.26 ± 0.13 [a] |

[a] A significant difference was observed by t test, in the biological activity of choriocarcinoma and pregnancy hCG, P=0.02

Figure 4

Table 3

|  | % penetration ± SD |
|---|---|
| Control cultures | 40 ± 10% (31, 40 and 51%) |
| Hyperglycosylated hCG, 10 ng/ml | 66 ± 13% (53, 68 and 78%) [a] |
| Regular hCG, 10 ng/ml | 34 ± 9% (26, 34 and 44%) [b] |

[a] A significant difference recorded in % penetration between control cultures and those with added hyperglycosylated hCG by t test (P=0.05).

[b] While no significant difference observed in % penetration between control cultures and those with added regular hCG, a significant difference was recorded by t test between those with added regular hCG and added hyperglycosylated hCG (P=0.025).

Figure 5

Table 4

| Additive | Number of cells<br>Mean ± SD<br>(increase over 70% confluency) |
|---|---|
| At 70% confluence, no additive | 2,300,000 ± 9090 |
| Further 24 hours, 2 µg/ml IgG | 4,600,000 ± 509,000 (1.98 ± 0.22 -fold) [a] |
| Further 24 hours, 2 µg/ml B152 | 3,000,000 ± 189,000 (1.32 ± 0.08 -fold) [a] |

[a] A significant difference was observed by t test, in the number of cells after 24 hours of culture with antibody B152, P=0.008. When considering number of cells at 70% confluency, a significant difference is observed by t test between fold increase with and without B152, P=0.008).

Size of Tumor (mean) Crosssectional area in mm$^2$

Weeks

FIGURE 10

Table 5. Measurement of total hCG, hCG/ITA free ß and ITA immunoreactivity in medium of JEG-3, JAR, BEWO, SWAN6, HKRT-11, and NTERA-2 cell lines, and $1^{st}$ and $3^{rd}$ trimester primary cultures of cytotrophoblast cells.

| Cell Line | Incubation time | ITA+ITA freeß ng/ml | free ß ng/ml | total hCG/ITA | ITA, % of total hCG |
|---|---|---|---|---|---|
| 1st trimester cytotrophoblast primary culture from terminated pregnancy | | | | | |
| | 24 | 6.7 | <0.1 | 6.5 | ~100% |
| 3rd trimester cytotrophoblast primary culture from term pregnancy | | | | | |
| | 24 | 2.2 | 0.2 | 2.0 | >90% |
| Cytotrophoblast and cancer cell lines | | | | | |
| SWAN6 | 72 | 27 | 1.2 | 27 | ~100% |
| HKRT-11 | 72 | 35 | 5 | 36 | <90% |
| NTERA-2 | 72 | 92 | 8.5 | 100 | >90% |
| JEG-3 | 48 | 24 | <0.1 | 20 | ~100% |
| JAR | 48 | 67 | 7 | 67 | >90% |
| BeWo | 48 | 135 | 45 | 159 | >80% |

Figure 12. Coomassie blue stained gel showing the ITAß affinity purified protein. Separated under reducing (left hand side) and non-reducing (right hand side) conditions.

METHOD FOR TREATING CANCER AND IDENTIFYING NOVEL ANTI-CANCER COMPOUNDS

RELATED APPLICATIONS

This application claims the benefit of priority of provisional applications U.S. 60/545,102, filed Feb. 17, 2004 and U.S. 60/577,683, filed Jun. 7, 2004, both of which applications are incorporated by reference in their entirety herein.

FIELD OF THE INVENTION

The present invention relates to compositions and methods for treating cancer, especially epithelial and eutopic cancers using inhibitors of hyperglycosylated hCG ("H-hCG") or β-H-hCG. In addition, the present invention relates to the inhibition of H-hCG as a contraceptive or abortifacient and method for reducing the risk of or terminating pregnancy in early pregnancy females.

BACKGROUND OF THE INVENTION

Human chorionic gonadotropin (hCG) measurement is the basis of all pregnancy tests. hCG is produced by trophoblast cells of the placenta in pregnancy. It is also produced by trophoblast cells in gestational trophoblastic diseases (hydatidiform mole, quiescent gestational trophoblastic disease and choriocarcinoma) and in testicular and other germ cell malignancies. hCG is a glycoprotein composed of 2 dissimilar subunits, α- and β-subunit, coded by separate genes on separate chromosomes, held together by charge interactions. hCG α-subunit is composed of 92 amino acids and contains 2 N-linked oligosaccharides. hCG β-subunit is composed of 145 amino acids and contains 2 N-linked and 4 O-linked oligosaccharides. The 8 oligosaccharide side chains comprise >30% of the molecular weight of hCG, making it an exceptionally highly glycosylated glycoprotein (1-7).

hCG is a heterogeneous molecule. Peptide variants, cleaved or nicked forms of hCG, free subunits of hCG, and fragments of hCG are all detectable in serum and urine samples during pregnancy (1). Oligosaccharide variants reflect availability of sugar substrates, and general cellular metabolism (7-9), expression of different glycosyltransferases by cells (8,9). It has long been recognized that the hCG molecule, particularly the β-subunit of hCG, produced in choriocarcinoma (trophoblastic cancer) and testicular germ cell cancer migrates slower than hCG β-subunit standards on electrophoresis gels and elutes earlier than hCG β-subunit standards from gel filtration columns (10-12). Both of these findings indicate a larger molecular weight molecule. This has long been assumed to be due to the presence of large oligosaccharides on hCG β-subunit (10-12). Further studies with lectins and structural studies have indicated the presence of larger or more complex oligosaccharides on choriocarcinoma hCG (3,4,13). In 1987, there was demonstrated a major difference between the 4 O-linked oligosaccharides on hCG in choriocarcinoma and normal pregnancy hCG. The hCG from 10 normal pregnancies primarily contained a mixture of tri- and tetrasaccharides, with 13% hexasaccharide (range 0 to 14%). In contrast, choriocarcinoma hCG preparations contained over 50% of the hexasaccharide structure (4,5). This observation was confirmed one year later by Amano et al (6).

In 1997 it was shown that the difference in the 4 O-linked oligosaccharides is the principal variation between choriocarcinoma and pregnancy hCG. While first trimester normal pregnancy urine hCG contained 12.3 to 19% (mean=15.6%) hexasaccharide structures, choriocarcinoma urine hCG contained 48 to 100% (mean=74.2%) hexasaccharide structures (7). A smaller change was observed in α-subunit and β-subunit N-linked oligosaccharides (from an average of 6.8% and 14% triantennary structures in first trimester pregnancy to 9.8% and 51% triantennary structures in choriocarcinoma, on α- and β-subunit respectively (7)). We call the hCG produced in choriocarcinoma H-hCG because of the large size due to overly large sugar units (14,15). Using an individual choriocarcinoma preparation with 100% hexasaccharide type O-linked oligosaccharides (C5 hCG), we generated in collaboration with Birken and colleagues a H-hCG-specific antibody (antibody B152) (16), and established an immunoassay using the C5 hCG calibrated by amino acid analysis as standard (14,16,17). This assay specifically detect the hexasaccharide O-linked oligosaccharides on the C-terminal of choriocarcinoma H-hCG (18). In 1998 O'Connor et al. used the B152-based assay to show that H-hCG is the principal form of hCG made during early pregnancy, in the weeks following implantation (17). This finding has now been confirmed by these and other investigators (14, 15,19-22). It has also been shown that early pregnancy H-hCG is the same size as choriocarcinoma H-hCG (18)

Root trophoblast cells, or cytotrophoblasts, are mostly phenotypically invasive cells. These are the principal cells in choriocarcinoma tumors and in blastocysts at the time of implantation (20,23,24). While cytotrophoblasts produce H-hCG, differentiated syncytiotrophoblast cells produce regular hCG (14,20). As published previously (15), H-hCG and its free β-subunit account for all of the hCG immunoreactivity in the conditioned medium of JAR, JEG-3 and BeWo choriocarcinoma cell lines. Lectin Western blot studies indicate that these cell lines produce hCG with very similar oligosaccharide structures to C5 choriocarcinoma hCG (10,25).

A standard was needed for the antibody B152-base H-hCG assay, other than an individual urine H-hCG (patient C5). Culture fluid from JEG-3 cell line was selected for this purpose because H-hCG consistently accounted for ~100% of the dimer immunoreactivity at 3 time points, reflecting sub-confluent and confluent culture densities and showing consistency with culture time (15). Large quantities of culture fluid were produced, and H-hCG was purified. The JEG-3 H-hCG is used as standard for the commercial H-hCG test (invasive trophoblast antigen or H-HCG test, Nichols Institute Diagnostics, San Clemente Calif.). While this standard has not yet been calibrated against W.H.O. hCG standards, or formally adopted by W.H.O. it is the only standard available.

hCG's primary function in pregnancy is to maintain progesterone production by corpus luteal cells, however, H-hCG may have an independent function. As published, the total hCG immunoreactivity in the conditioned medium of JAR choriocarcinoma cells is H-hCG and its free β-subunit (15). Studies by Lei et al. (26), show that JAR cells are invasive in Matrigel membrane inserts in vitro, and are rapidly tumorigenic when transplanted into athymic nude mice in vivo. Lei et al. (26) treated JAR cells with hCG α-subunit antisense cDNA. This blocked secretion of the H-hCG and its free β-subunit. It also blocked Matrigel membrane insert invasion and tumorigenesis in athymic nude mice.

Objects of the Invention

It is an object of the invention to provide methods of inhibiting H-hCG and/or β-H-hCG in order to reduce the likelihood that a cancer will spread or to treat cancer.

It is another object of the invention to provide methods of reducing the likelihood of and/or terminating a pregnancy using an inhibitor of H-hCG and/or β-H-hCG according to the present invention.

It is an additional object of the invention to provide inhibitors of H-hCG and/or β-H-hCG in order to treat cancer.

It is still a further object of the present invention to provide methods to identify inhibitors of H-hCG and/or β-H-hCG to be used to treat and/or prevent cancer or as a contraceptive or abortifacient to prevent and/or terminate a pregnancy.

It is yet another object of the invention to provide vaccines and methods to immunize patients to reduce the likelihood that the patient will contract cancer.

Another object of the invention relates to the use of inhibitors of H-hCG and/or β-H-hCG to increase the likelihood that a cancer will remain in remission and reduce the likelihood of a recurrence of cancer.

Any one or more of these and/or other objects of the invention may be readily gleaned from a description of the invention which follows.

SUMMARY OF THE INVENTION

It has now been discovered that the inhibition of H-hCG and/or β-H-hCG can be used as an effective method for the treatment of cancer in patients in need of anti-cancer therapy. In addition, the present invention relates to the use of H-hCG and/or β-H-hCG inhibitors as an abortifacient and/or contraceptive in a birth control method.

In aspects of the present invention, inhibitors of H-hCG and/or β-H-hCG may be used to inhibit the growth, formation and/or metastasis of cancer, especially including cancerous tumors.

In particular aspects of the present invention, humanized or non-immunogenic murine polyclonal and/or monoclonal antibodies reactive with H-hCG and/or β-H-hCG are used in effective amounts to treat cancer, alone or in combination with other traditional anti-cancer agents. These same antibodies or other antibodies may be used to prevent and/or terminate an unwanted pregnancy in a woman suspected of or at risk for becoming pregnant.

In further aspects of the present invention, a method of identifying a potential anti-cancer agent as an inhibitor of H-hCG and/or β-H-hCG at a cancer cell is described. The method comprises growing cancer cells in the presence of H-hCG and/or β-H-hCG and then determining whether a test compound inhibits the growth of the cancer cells by comparing the growth of the cancer cells grown in the presence of H-hCG and/or β-H-hCG in the presence or absence of a test compound. These same compounds may also find use as contraceptives and/or abortifacients for preventing or terminating an unwanted pregnancy.

The present invention also relates to methods of identifying compounds which inhibit the expression of H-hCG and/or β-H-hCG from cancer cells. The invention encompasses the idea that modulating the cellular H-hCG or β-H-hCG expression will be useful in inhibiting H-hCG and/or β-H-hCG binding to cancer cells, thus inhibiting further growth of the cancer and acting as a means of treating the cancer, and that a whole new class of anti-H-hCG or anti-β-H-hCG compounds can be developed as a result of this discovery, e.g., those which block cancer cell proliferation pathways.

The present invention includes novel mechanisms for the development of anticancer compounds which target cellular functions essential for cancer cell growth. The invention also includes novel anticancer compounds and methods of their use. These anticancer compounds are designed primarily to disrupt cellular processes for the production of H-hCG and/or β-H-hCG in cancer cells, in order to inhibit the effect of H-hCG and β-H-hCG in increasing cancer cell growth. However, as is described in greater detail below, the invention also encompasses methods of inhibiting the binding of H-hCG and β-H-hCG to cancer cells and inhibit cancer cell growth and/or metastasis as well as the identification and use of compounds which inhibit H-hCG and β-hCG production/formation pathways.

In certain aspects of the present invention, i.e., in those aspects related to the prevention/termination of pregnancy using an inhibitor of H-hCG and/or β-H-hCG, the inhibitor acts primarily to inhibit implantation of a fertilized ovam (blastocyst) to the endometrium and its subsequent embedding in the compact layer, generally occurring 6 or 7 days after fertilization of the ovum. The prevention of implantation results in the termination of an unwanted pregnancy.

Still another aspect of the invention is the use of H-hCG and/or β-H-hCG or an immunogenic fragment or immunogenic variant thereof to prepare vaccines and/or immunogenic compositions to reduce the likelihood of a mammalian contracting cancer, reducing the likelihood of further growth or metastasis of a cancer, or reducing the likelihood of a recurrence of cancer in a patient whose cancer is in remission. Methods of immunizing mammals against cancer using the vaccines as described above represent another aspect of the present invention.

Other aspects of the present invention relate to the use of one or more of an inhibitor of H-hCG or β-H-hCG to be used as an abortifacient in a birth control method. In this method, a woman who is suspected of being pregnant or who is at risk for becoming pregnant is administered one or more of the inhibitors of H-hCG or β-H-hCG which are otherwise disclosed in the present invention in an effective amount shortly after intercourse in order to avoid an unwanted pregnancy.

BRIEF DESCRIPTION OF THE FIGURES

FIG. 1 shows the primary structure of the α-(SEQUENCE ID No: 1 and β-subunits (SEQUENCE ID NO: 2) of hCG with carbohydrate attachment sites. See, Morgan, et al., *J. Biol. Chem.*, 250, 5247-5258 (1975). The numbers are in amino acid sequence order. N indicates asparagines residues with N-linked oligosaccharides, and O indicates serine residues with O-linked glycans. Arrows (↑) denote sites of potential amino-terminal heterogeneity and nicking of internal peptide bonds. Molecular weight for α-subunit calculated calculated based on an intact primary sequence, five disulfide bonds, one sialylated monoantennary and one sialylated biantennary.

FIG. 2 (Table 1) shows the production of regular and H-hCG in pregnancy, and trophoblast disease and cancer patient serum and urine. H-hCG and total hCG are measured and the proportion of immunoreactivity due to H-hCG calculated (H-hCG÷total hCG) calculated. Legend:[a] A significant difference was observed between the proportion of total hCG immunoreactivity due to hyperglycosylated hCG in benign gestational trophoblastic diseases (partial and complete mole, and quiescent gestational trophoblastic disease) and in invasive disease (choriocarcinoma and testicular germ cell) in serum samples P<0.00001 and urine sample P>0.0001.

[b] A significant decline is found in serum samples between the 3rd and 6th complete week (P=0.004), and in urine samples between the 4th and 7th complete week (P<0.00005) and between the first and the third trimesters of pregnancy (P=0.02).

FIG. 3 (Table 2) shows the biological activity of purified regular and H-hCG from cases with pregnancy and trophoblast diseases. All results are those using hCG preparations described previously (5-7). For oligosaccharide composition, 3 percentages values are listed as %, %, %. These correspond to the percentage of larger oligosaccharides found N-linked to α-subunit (triantennary and fucosylated oligosaccharides), to β-subunit (triantennary oligosaccharides), and O-linked to β-subunit (hexasaccharide structures), respectively, as published previously 5-7). cAMP production was measured in rat corpus luteal cells. Activity was determined as pmol cAMP/mg cell protein/ng hCG immunoreactivity. All determinations are averages of triplicate measurements at 4 concentrations of hCG immunoreactivity.

FIG. 4 shows the action of H-hCG and regular hCG on cytotrophoblast invasion of Matrigel membranes. Isolated cytotrophoblast cells were prepared from term placenta, and then cultured 24 hours on Matrigel membranes and control inserts. Control cytotrophoblast cultures produced 2.3 ng/ml of H-hCG total in a 24 hour period. The experiment was repeated in triplicate using medium containing excess hyperglycosylated or regular hCG (10 ng/ml), or no additive (controls). Cell penetration of membranes were photographed and counted. Cell penetration was compared with that of control inserts. The percentage penetration or invasion was calculated using the formula described by the manufacturer.

FIG. 5 shows the effect of monoclonal antibody B152 (anti-H-hCG) on JEG-3 choriocarcinoma cell line medium H-hCG concentration, and on cell growth. All values were measured from quadruplicate cultures, grown to 70% estimated confluence in the absence of antibody. At this time, a proportion of cultures were washed and cells counted. Further culture flasks were then cultured for an additional 24 hours with non-specific IgG (controls), or 24 hours in the presence of antibody B152. At this time cultures were washed and cells counted.

Figure 6:
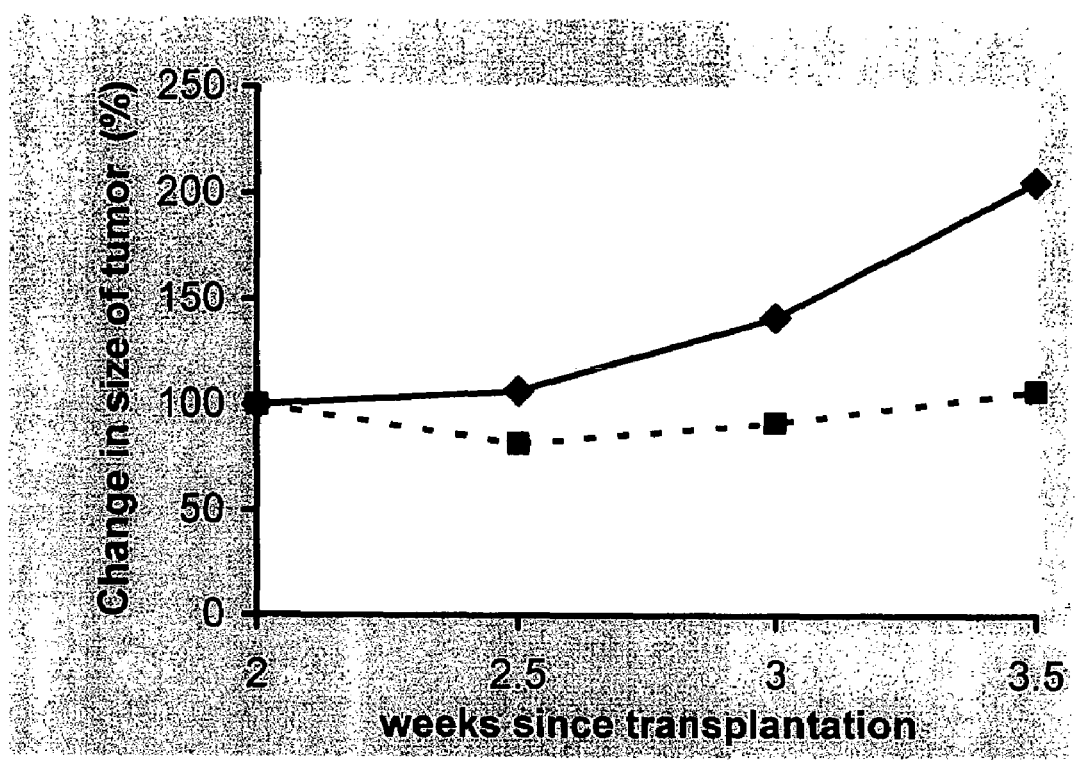

FIG. 6 shows the effect of anti-H-hCG antibody B152 on tumor growth and progression. Athymic nude mice were subcutaneously transplanted with JEG-3 choriocarcinomas cells. After subcutaneous tumor clearly visible (2 weeks), mice were either treated with intraperitoneal injections, twice each week, with non-specific IgG (controls, solid diamonds and solid line) or with B152 (solid squares, dashed lines). Results are average results with 6 mice. In the control group, relative tumor size was 100%, 107±22%, 142±43% and 206±53%, and in those given B152 was, 100%, 82±11%, 92±11% and 108±11%, respectively, for weeks 2, 2.5, 3 and 3.5 following transplantation. Using a t test a significant difference was noted between all the changes at all time points (2.5, 3 and 3.5 weeks) with the B152-treated and the control mice (P=0.003). While a correlation between time and growth was observed with the control group ($r^2$=0.97), none was observed with the B152-treated mice ($r^2$=0.15).

Figure 7:
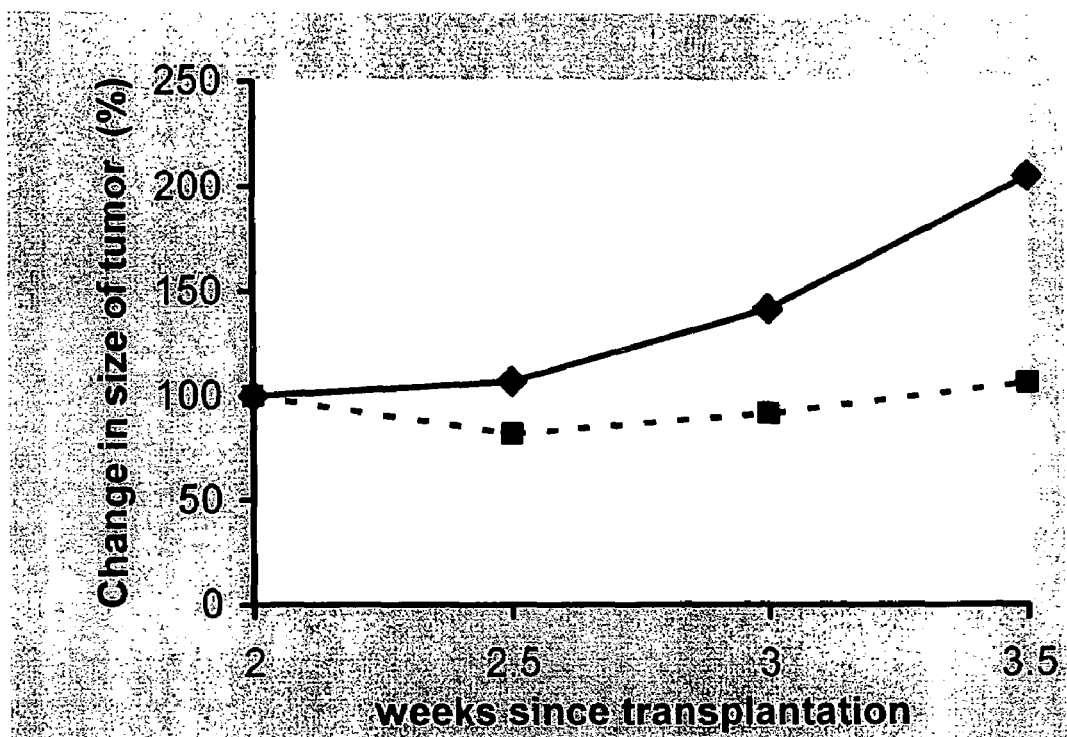

FIG. 7 shows the effect of anti-H-hCG antibody B152 on tumorigenesis. Athymic nude mice were subcutaneously transplanted with JEG-3 choriocarcinomas cells. Starting with the time of transplanting, mice were either treated with intraperitoneal injections, twice each week, with non-specific IgG (controls, solid diamonds and solid line) or with B152 (solid squares, dashed lines). Results are average results with 11 mice. In those given non-specific IgG, cross section size of tumor was 0, 0, 79±58, 121±68 and 149±98 mm², and those given B152 was 0, 0, 13±7.6, 27±15 and 43±22 mm², respectively, for weeks 0, 1, 2, 3 and 4 following transplantation. A significant difference was observed by t test at 2, 3 and 4 weeks, P=0.0071, 0.0031 and 0.012, respectively.

Figure 8:
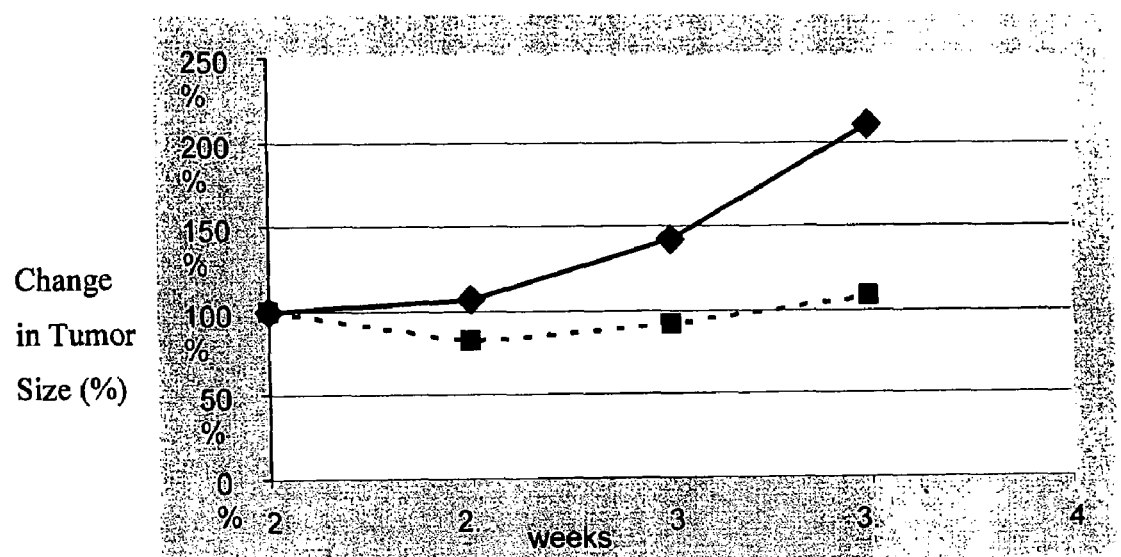

FIG. 8 shows the effects of anti-H-hCG monoclonal on tumor growth. Nude mice were transplanted with JEG-3 choriocarcinomas cells, after tumor establishment (2 weeks), treated with non-specific IgG (controls, solid line) and with B152 anti-H-hCG (dashed lines).

Figure 9:
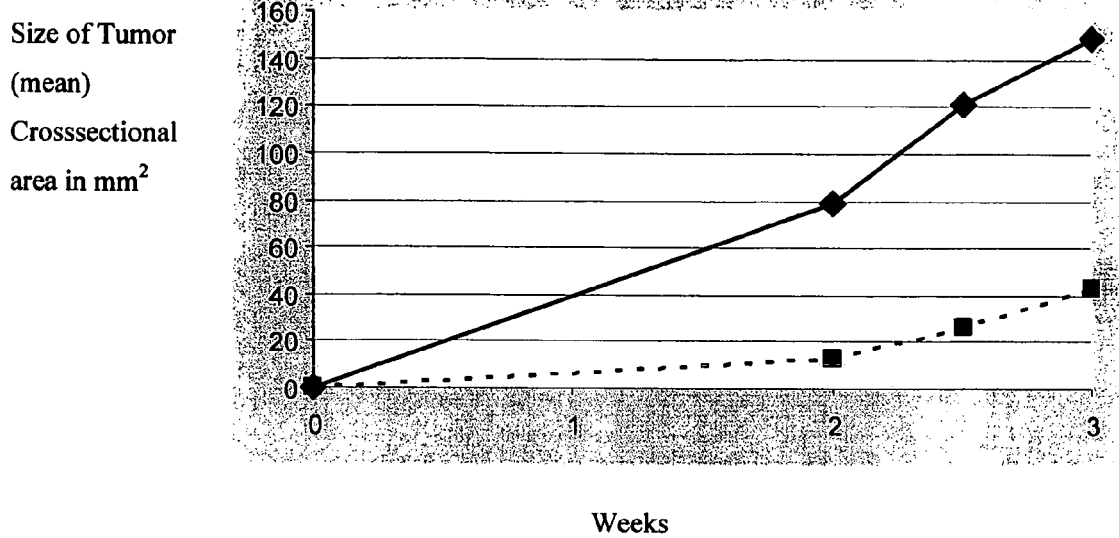

FIG. 9 shows the effects of nude mice treated with IgG (controls, solid line) and with B152 anti-H-hCG (dashed lines) after transplantation of JEG-03 choriocarcinoma cells, or during tumorigenesis FIG. 10 shows the measurement of total hCG, hCG/H-hCG free β and H-hCG immunoreactivity in medium of JEG-3, JAR, BEWO, SWAN6, HKRT-11, and NTERA-2 cell lines, and $1^{st}$ and $3^{rd}$ trimester primary cultures of cytotrophoblast cells.

Figure 11:
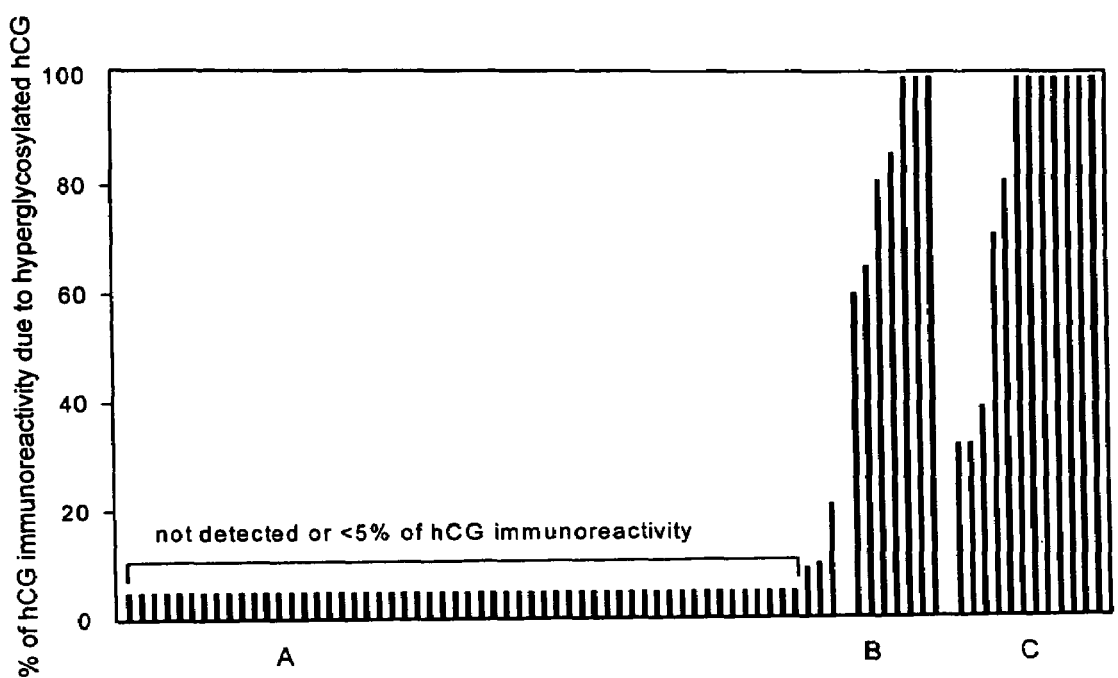

FIG. 11 shows total hCG and H-hCG measured in serum from women with trophoblast disease. These included 57 cases with quiescent GTD or non-invasive disease (group A). It also included 7 cases with multi-year history of quiescent GTD that became invasive (shown by sharply rising hCG/imaging methods/pathology) (group B), and 15 other cases with proven invasive trophoblastic disease (GTN and choriocarcinoma) (group C).

Figure 12:
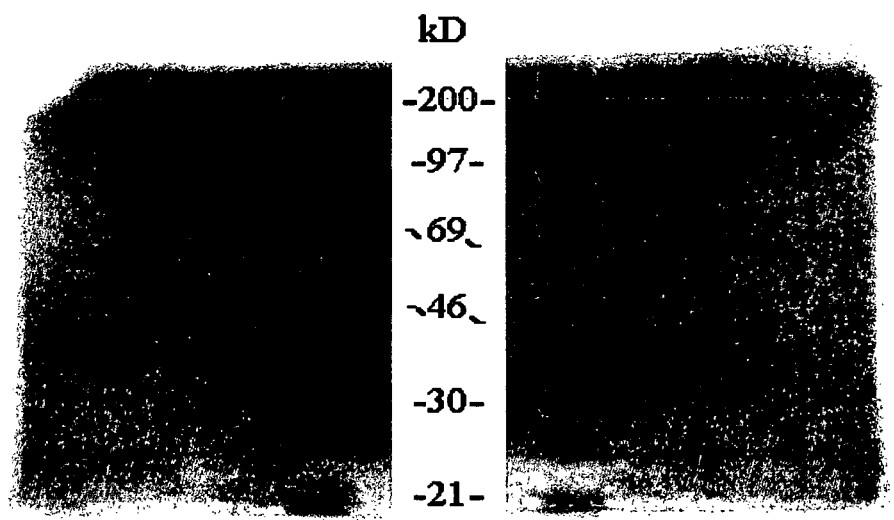

FIG. 12 shows coomassie blue stained gel showing the H-hCGβ affinity purified protein. Separated under reducing (left hand side) and non-reducing (right hand side) conditions.

Figure 13:
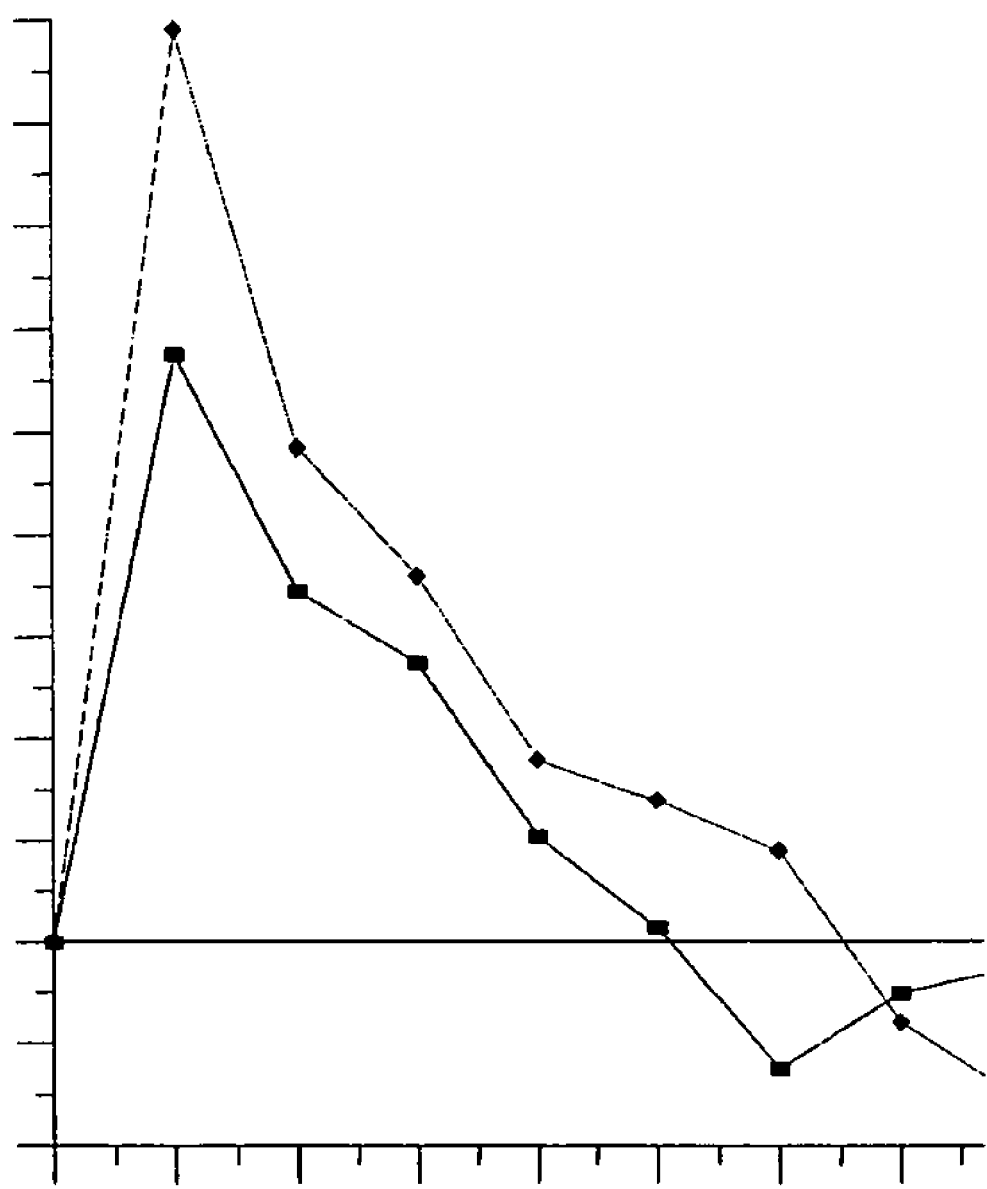

FIG. 13 shows the percentage change in nucleosome concentration from the control following TGFβ and H—HCGβ coincubation with the bladder carcinoma cell lines 5637 (———, square) and T24 (- - -, diamond). 100 pmol/ml TGFβ (to initiate apoptosis) was incubated with cells. Plot shows coincubation with increasing concentrations of H-HCGβ (to negate the TGFβ effect). Graph miniaturized, X axis is H-HCGβ concentration (0 to 400 pmol/ml), and Y axis is change in nucleosome enrichment factor per cell relative to control (0 to 280%).

Figure 14:
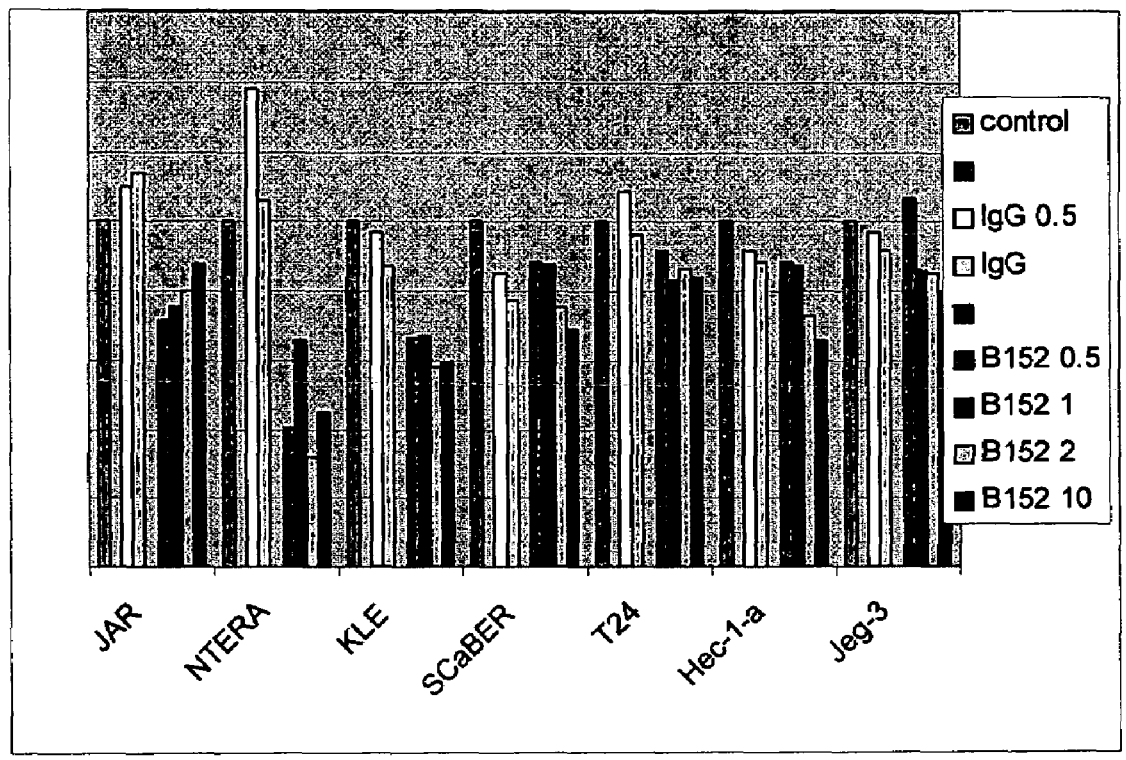

FIG. 14 (graph of Table 6) shows that when cancer cells are cultured with increasing concentrations of monoclonal antibody B152 (against H-hCG) the cells are increasingly inhibited from growing. All values are expressed as a percentage of cell growth compared to the effect of an equivalent concentration of non-specific mouse antibody.

DETAILED DESCRIPTION OF THE INVENTION

The following terms shall be used to describe the present invention. In the absence of a specific definition set forth herein, the terms used to describe the present invention shall be given their common meaning as understood by those of ordinary skill in the art.

The term "patient" is used throughout the specification to describe an animal, preferably a mammal, more preferably a human, to whom treatment or method according to the present invention is provided. For treatment of those infections, conditions or disease states which are specific for a specific animal such as a human patient, the term patient refers to that specific animal.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal and to cause the death of the patient unless adequately treated. As used herein, the term cancer is used to describe all cancerous disease states applicable to treatment according to the present invention and embraces or encompasses the pathological process associated with all virtually all epithelial cancers, including carcinomas malignant hematogenous, ascitic and solid tumors. Representative cancers include, for example, stomach, colon, rectal, liver, pancreatic, lung, breast, cervical, uterine, ovary, prostate, testis, bladder, renal, brain/CNS, head and neck, throat, Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' Tumor, neuroblastoma, hairy cell leukemia, mouth/pharynx, oesophagus, larynx, kidney, among others, which may be treated by one or more compounds according to the present invention. The present invention may be used preferably to treat eutopic cancers such as choriocarcinoma, testicular choriocarcinoma, non-seminomatous germ cell testicular cancer, placental cancer (trophoblastic tumor) and embryonal cancer, among others.

The term "effective amount" is used throughout the specification to describe an amount of the present composition which is used to effect an intended result when used in the method of the present invention. In numerous aspects of the present invention the term effective amount is used in conjunction with the treatment of a patient suffering from neoplasia, in preferred embodiments, a cancerous tumor to prevent the further growth of the cancer, to bring that growth under control and/or preferably, produce a remission of the cancer. In other aspects, the term effective amount simply refers to an amount of an agent which produces a result which is seen as being beneficial or useful, including in methods according to the present invention where the identification of an inhibitor of H-hCG and/or β-H-hCG is sought, or the use of such an inhibitor as an abortifacient and/or contraceptive to prevent or reduce the likelihood of an unwanted pregnancy.

The term effective amount with respect to the presently described compounds and compositions is used throughout the specification to describe that amount of the compound according to the present invention which is administered to a mammalian patient, especially including a human patient, suffering from cancer, to reduce or inhibit the growth or spread (metastasis) of the cancer, and in particular, a cancer or malignant tumor of epithelial tissue. Preferably, treatment with the compounds described in the present invention will result in a remission of the malignant hematogenous, ascitic or solid tumor. In the case of solid tumors, in certain preferred aspects, the compounds according to the present invention will inhibit the further growth of the cancer/tumorous tissue and shrink the existing cancer/tumor.

In other embodiments, in particular methods of preventing or terminating unwanted pregnancies, the term effective amount is used to describe amounts of inhibitors of H-HCG and/or β-H-HCG which may be used to reduce the likelihood of a pregnancy or to terminate an unwanted pregnancy.

The term "hyperglycosylated hCG", "H-hCG", "invasive trophoblast antigen" or "ITA" are used synonymously throughout the specification to describe a glycoprotein hormone secreted by trophoblast cells of the placenta of pregnant women and by cancer cells. H-hCG is similar to C5 hCG, which is a nicked H-hCG obtained from a choriocarcinoma patient. H-hCG, as defined, also includes fragments of H-hCG, or variants of H-hCG. In particular, H-hCG encompasses molecules that exhibit similar biological activities or expression patterns to H-hCG and that exhibit aberrant carbohydrate levels as compared to normally glycosylated hCG including, nicked hCG, β-subunits of hyperglocosylated hCG ("β-H-hCG"), or any combination thereof. Examples of H-hCG isoforms include isoforms that comprise 57% triantennary N-linked oligosaccharides and 68% hexasaccharide-type O-linked oligosaccharides. Another H-hCG isoform may comprise 48% triantennary N-linked oligosaccharides and 100% hexasaccharide-type O-linked oligosaccharides or alternatively, for example during pregnancy, a relatively small proportion of more complex triantennary N-linked oligosaccharides (0-30%) and larger hexasaccharide-type O-linked sugar units (0-20%) are also found. Representative chemical structures of H-hCG and β-H-hCG are set forth in attached FIG. 1.

The term "antibody" shall mean an antibody, or an antigen-binding portion thereof, that binds to H-hCG and/or β-H-hCG or fragments or variants thereof as defined herein with a high degree of specificity (i.e., "binds specifically" to the antigen of interest, but not to other antigens of similar structure, thus reducing side effects or negative interactions) and prevents the interaction of H-hCG or β-H-hCG with target cells at their site of activity, such as, for example, cancer cells to treat cancer or endometrial cells, among others to prevent an unwanted pregnancy. H-hCG or β-H-hCG antibodies can be used therapeutically to modulate or inhibit the binding of H-hCG or β-H-hCG with cancer cells. An H-hCG ("anti-H-hCG") or β-H-hCG ("anti-β-H-hCG") antibody may be polyclonal or monoclonal and is preferably a human antibody or a humanized (i.e., non-immunogenic non-human antibody, for example, murine, rat or rabbit which can be administered to a human without eliciting an immunogenic response against itself in the host) antibody. Preferably, the antibody is specific for binding H-hCG and/or β-H-hCG as defined herein without binding to other proteins or hormones such as hCG or β-hCG which have different functions in the patient. Methods for making polyclonal and monoclonal antibodies are well known to the art. Monoclonal antibodies can be prepared, for example, using hybridoma techniques, recombinant, and phage display technologies, or a combination thereof. See, for example, Golub et al., U.S. Patent Application Publication No. 2003/0134300, published Jul. 17, 2003, for a detailed description of the preparation and use of antibodies as diagnostic or therapeutic agents. Antibodies to hCG isoforms, such as H-hCG, can be generated by standard means as described, for example, in "Antibodies: A Laboratory Manual" by Harlow and Lane (Cold Spring Harbor Press, 1988), which is hereby incorporated by reference.

Preferably, the antibody is a monoclonal antibody to provide the desired specificity of binding to H-hCG or β-H-hCG as defined herein without binding appreciably to, for example, hCG or β-hCG. A useful antibody which selectively binds H-hCG includes Antibody B152 (ATCC No. HB-12467), described in U.S. Pat. Nos. 6,339,143 and 6,429,018, both of which references are incorporated by reference herein, although these antibodies are not "humanized" and are therefore less preferred because they are mouse monoclonal antibodies. These antibodies may be humanized using techniques which are well-known in the art. These mouse antibodies are more useful in analyzing for inhibitors of the formation of H-hCG in the present invention.

In the therapeutic aspects of this invention, the antibody is preferably a human or humanized antibody. A human antibody is an antibody having the amino acid sequence of a human immunoglobulin and includes antibodies produced by human B cells, or isolated from human sera, human immunoglobulin libraries or from animals transgenic for one or more human immunoglobulins and that do not express endogenous immunoglobulins. Approaches to these preferred antibodies are described in for example, U.S. Pat. No. 5,939,598 by Kucherlapati et al., among numerous others, including for example, U.S. Pat. Nos. 5,530,101; 5,614,611 and 5,562,611, as well as U.S. Pat. No. 6,827,934, which describe general and more specific methods which can be applied to the present invention, relevant portions of which are incorporated by reference herein. Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge, in this case with H-HCG or β-H-HCG (see, e.g., Jakobovits et al., Proc. Natl. Acad. Sci. U.S.A., 90:2551-2555 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)). Production of H-hCG or β-H-hCG and the corresponding antibodies follows well-known methods described in the art.

Antibodies generated in non-human species can be "humanized" for administration in humans in order to reduce their antigenicity. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Residues from a complementary determining region (CDR) of a human recipient antibody are replaced by residues from a CDR of a non-human species (donor antibody) such as mouse, rat or rabbit having the desired specificity. Optionally, Fv framework residues of the human immunoglobulin are replaced by corresponding non-human residues. See Jones et al., Nature, 321:522-525 (1986); Riechmann et al., Nature, 332:323-327 (1988); and Presta, Curr. Op. Struct. Biol., 2:593-596 (1992). Methods for humanizing non-human antibodies are well known in the art. See Jones et al., Nature, 321:522-525 (1986); Riechmann et al., Nature, 332:323-327 (1988); Verhoeyen et al., Science, 239:1534-1536 (1988); and (U.S. Pat. No. 4,816,567), among others.

The term "H-hCG inhibitor and/or β-H-hCG inhibitor", as described in the present specification shall mean antibodies, polynucleotides, polypeptides, compounds, compositions or other agents which specifically inhibit the expression or production of H-hCG and/or β-H-hCG directly or indirectly or the binding of H-hCG and/or β-H-hCG on target cells to prevent H-hCG and/or β-H-hCG from eliciting a biological response in the treatment of cancer. In the case of embodiments of the present invention which are directed to preventing or terminating an unwanted pregnancy, the use of short-term direct inhibitors of H-hCG and/or β-H-hCG such as polyclonal or monoclonal antibodies, are preferred. Antibodies as otherwise described herein are considered inhibitors of H-hCG and/or β-H-hCG for purposes of the present invention because they bind to H-hCG and/or β-H-hCG and prevent H-hCG/β-H-hCG binding to target cells where they would normally elicit a biological response. Other inhibitors of H-hCG and/or β-H-hCG include inhibitors of the expression or production of H-hCG and/or β-H-hCG in cancer cells (whether that production is the actual polypeptide synthesis of hCG or its β-subunit, or the formation of hCG or its β-subunit by glycosylation or other biochemical step), which method can comprise the introduction of an expression vector encoding for an anti-sense nucleotide or other agent which would prevent the expression of hCG or other precursor of H-hCG or β-H-hCG or the formation of H-hCG or β-H-hCG.

In making antibodies or using antibodies against H-hCG and/or β-H-hCG for use in the present invention methods which are readily recognized by those of ordinary skill are used. The generation of polyclonal antibodies is accomplished by inoculating the desired animal with the antigen and isolating antibodies which specifically bind the antigen therefrom.

Monoclonal antibodies may be used extracellularly or intracellularly to effect inhibition of the binding of H-hCG and/or β-H-hCG. Monoclonal antibodies can be used effectively intracellularly to avoid uptake problems by cloning the gene and then transfecting the gene encoding the antibody. Such a nucleic acid encoding the monoclonal antibody gene obtained using the procedures described herein may be cloned and sequenced using technology which is readily available in the art.

Monoclonal antibodies directed against full length or peptide fragments of H-hCG or β-H-hCG or an appropriate fragment thereof may be prepared using any well known monoclonal antibody preparation procedure. Quantities of the desired peptide may also be synthesized using chemical synthesis technology. Alternatively, DNA encoding the desired peptide may be cloned and expressed from an appropriate promoter sequence in cells suitable for the generation of large quantities of peptide. A number of cancer cell lines may be used to produce H-hCG or β-H-hCG. These can be produced by cytotrophoblast cells and invasive trophoblast cells of pregnancy or choriocarcinoma, among others. One method involves transfecting cells of this nature with a vector which can hyperexpress hCG or β-hCG. Once produced, the polypeptide is then hyperglycosylated in the cells and isolated. Monoclonal antibodies directed against the immunogen are generated from mice or other appropriate animal immunized with the immunogen using standard procedures as referenced herein. A nucleic acid encoding the monoclonal antibody obtained using the procedures described herein may be cloned and sequenced using technology which is available in the art. Further, the antibody of the invention may be "humanized" using the existing technology known in the art.

Alternatively, antibodies or fragments which bind to H-hCG and/or β-H-hCG produced in viruses (phage antibodies) may be used. This technique is well known in the art. To generate a phage antibody for use in the present invention, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suH-hCGble bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such planning techniques are well known in the art and are described for example, in Wright et al., *Crit Rev Immunol.* 1992; 12(3-4): 125-68.

Processes such as those described above, have been developed for the production of human antibodies using M13 bacteriophage display (Burton et al., 1994, Adv. Immunol. 57:191-280) and may be used in the present invention. Essentially, a cDNA library is generated from mRNA obtained from a population of antibody-producing cells. The mRNA encodes rearranged immunoglobulin genes and thus, the cDNA encodes the same. Amplified cDNA is cloned into M 13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) may also be used to create inhibitors for use in the present invention. Fab molecules comprise the entire Ig light chain, that is, they comprise both the variable and constant region of the light chain, but include only the variable region and first constant region domain (CHl) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, *J. Mol. Biol.* 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Krulf et al. 1995, J. Mol. Biol. 248:97-105).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

In certain embodiments, the present invention relates to the use of an inhibitor of H-hCG or β-H-hCG for the treatment of cancer in mammals, especially humans. In addition, such inhibitors may be used to prevent or terminate an unwanted pregnancy in a female at risk to become or who is pregnant. As it has been discovered that H-hCG and/or β-H-hCG are responsible for the growth and metastasis of tumors and cancer in patients, it is an effective treatment of cancer to provide to a cancer patient in need of therapy an effective amount of an H-HCG or β-H-HCG inhibitor to that patient. The inhibitor of H-hCG or β-H-hCG according to the present invention may take the form of an antibody which binds to H-hCG or β-H-hCG, thus, preventing the H-hCG or β-H-hCG from promoting the growth and/or the spread of cancer in the patient, an anti-sense polynucleotide which prevents or inhibits the expession of hCG and/or β-hCG and consequently, the formation of H-hCG or β-H-hCG, or a small molecule inhibitor which prevents the formation of H-hCG or β-H-hCG within cancer cells. In another embodiment, the present invention relates to a method of identifying inhibitors of H-hCG and/or β-H-hCG in cancer cells, which are useful as anti-cancer agents having a novel mechanism of action.

Using Antibodies to Inhibit the Action of H-hCG

The invention includes a method by which antibodies can be generated and used as inhibitors of H-hCG or β-H-hCG interactions with cancer cells which function to enhance the growth and spread of cancer. The preparation and use of antibodies to inhibit protein function is a technique known by those skilled in the art. The generation of polyclonal antibodies is accomplished by inoculating the desired animal with the antigen and isolating antibodies which specifically bind the antigen therefrom, preferably specifically, i.e., to the substantial exclusion of other antigens.

Monoclonal antibodies can be used effectively intracellularly to avoid uptake problems by cloning the gene for the antibody and then transfecting the gene encoding the antibody. Such a nucleic acid encoding the monoclonal antibody gene obtained using the procedures described herein may be cloned and sequenced using technology which is available in the art. This is an appropriate methodology for the treatment of cancer or the prevention (reducing the likelihood) of a recurrence of cancer after remission.

Monoclonal antibodies directed against full length or peptide fragments of H-hCG or β-H-hCG may be prepared using any well known monoclonal antibody preparation procedure. Quantities of the desired peptide precursor hCG or β-hCG may also be synthesized using chemical synthesis technology and then exposed to cancer cells. Alternatively, DNA encoding the desired peptide(s) may be cloned and expressed from an appropriate promoter sequence in cells suitable for the generation of large quantities of peptide, transfected into cancer cells wherein glycosylation will occur producing H-hCG or β-H-hCG, each of which can be readily isolated using techniques which are well known in the art. Monoclonal antibodies directed against the peptide may be generated from mice immunized with the peptide using standard procedures as referenced herein. A nucleic acid encoding the monoclonal antibody obtained using the procedures described herein may be cloned and sequenced using technology which is available in the art. Further, the antibody of the invention may be "humanized" using the existing technology known in the art.

By way of example, to generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suH-hCGble bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such techniques are well known in the art and are described for example, in Wright et al., Crit Rev Immunol. 1992; 12(3-4): 125-68, (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M 13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies, but rather any antibody which can bind H-hCG or β-H-hCG. Advantageously, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CHI) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention may also be construed to include synthetic phage display libraries in which the heavy and light chain variable regions may be synthesized such that they include nearly all possible specificities (Barbas, 1995, Nature Medicine 1:837-839; de Krulf et al. 1995, J. Mol. Biol. 248:97-105).

The present also includes antibodies which are synthetic in nature. By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "vaccine" as used herein is defined as material used to provoke an immune response after administration of the materials to a mammal and thus conferring immunity.

The term "immunogen" is used to describe H-hCG and/or β-H-hCG or a polypeptide fragment thereof (which may be injected into a patient directly or which may be produced within the patient from an expression vector, or alternatively used to generate antibodies to H-hCG and/or β-H-hCG, and in particular, an epitope on these molecules) which provokes an immune response (humoral or cell-based) in a mammal. The test of an immunogenic response, may be determined by in vitro and in vivo techniques which are well-known in the art, for example, as described in U.S. Pat. Nos. 6,740,324 and 6,716,623, or as otherwise described in the art.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions.

The term "adjuvant" is used to describe a compound or composition which is added to an immunogenic polypeptide in a vaccine in order to boost an immunogenic response to the immunogenic polypeptide. Representative adjuvants such as muramyl dipeptide derivatives (MDP) or analogs that are described in U.S. Pat. Nos. 4,082,735; 4,082,736; 4,101,536; 4,185,089; 4,235,771; and 4,406,890 may be used. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic.RTM.), a non-ionic surfactant, and a metabolizable oil such as squalene (U.S. Pat. No. 4,606,918).

Inhibiting H-HCG or β-H-HCG Using Antisense Technique

In a further embodiment, antisense nucleic acids complementary to H-hCG or β-H-hCG precursor (especially, hCG and β-hCG) mRNA can be used to block the expression or translation of the corresponding mRNAs. For example, antisense nucleic acids complementary to hCG or β-hCG-iRNAs can be used to block H-hCG or β-H-hCG function by inhibiting translation of the precursor peptide hCG or β-hCG and this can be done by transfecting a gene with the appropriate sequence linked to a promoter to control its expression. hCG and β-hCG genes have been sequenced and based on this data-antisense nucleic acids can be readily prepared and expressed in human cells using techniques known to those skilled in the art.

Antisense oligonucleotides as well as expression vectors comprising antisense nucleic acids complementary to nucleic acids encoding H-hCG or β-H-hCG can be prepared and used based on techniques routinely performed by those of skill in the art. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497). This invention should not be construed to include only poly/oligonucleotides antisense to hCG and β-hCG, but any other polypeptide precursor of H-hCG or β-H-hCG to which an antisense poly/oligonucleotide may be used and should not be construed to include only these particular antisense methods described.

Oligonucleotides which contain at least one phosphorothioate modification are known to confer upon the oligonucleotide enhanced resistance to nucleases. Specific examples of modified oligonucleotides include those which contain phosphorothioate, phosphate or phosphonate ester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. 5,034,506) or polyamide backbone structures (Nielsen et al., 1991, Science 254: 1497) may also be used in the present invention to prepare antisense oligonucleotides.

The examples of oligonucleotide modifications described herein are not exhaustive and it is understood that the invention includes additional modifications of the antisense oligonucleotides of the invention which modifications serve to enhance the therapeutic properties of the antisense oligonucleotide without appreciable alteration of the basic sequence of the antisense oligonucleotide.

The oligonucleotide inhibitors of hCG and β-hCG can be used independently and administered to a cancer patient parenterally. The phosphorothioate oligonucleotides enter cells readily without the need for transfection or electroporation. Once inside the cells, the PT-oligonucleotides may hybridize with the nascent mRNA very close to the transcriptional start site, which is usually a good site for maximum effect of antisense oligonucleotide inhibition. Suppression of intracellular hCG or β-hCG expression in cancer cells has been shown to be possible and represents a potential approach to the treatment of cancer in patients in need of such therapy.

Inhibiting H-hCG or β-H-hCG Protein Pathway

The chemical structure of H-hCG or β-H-hCG (FIG. 1) suggests that hCG and β-hCG are required for H-hCG or β-H-hCG activation. The invention therefore also relates to the inhibition of hCG and β-hCG protein-formation pathways as well as hCG and β-hCG glycolyation pathways to form H-hCG or β-H-hCG in cancer cells by inhibitors, especially including small molecules.

The method of the invention is useful for inhibiting growth and metastasis of cancer cells which are dependent upon H-hCG or β-H-hCG for that growth or spread. The method is not limited to only those cancers described herein, and should be construed to include any cancer cell which utilizes H-hCG or β-H-hCG for enhancing growth and/or its spread in a patient. The method should also be construed to include livestock, pets and humans.

The present invention may be used to treat epithelial cancers, including carcinomas, malignant hematogenous, ascitic and solid tumors. Representative cancers which may be treated in the present invention include, for example, stomach, colon, rectal, liver, pancreatic, lung, breast, cervical, uterine, ovary, prostate, testis, bladder, renal, brain/CNS, head and neck, throat, Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' Tumor, neuroblastoma, hairy cell leukemia, mouth/pharynx, oesophagus, larynx, kidney, among others. The present invention may be used preferably to treat eutopic cancers such as choriocarcinoma, testicular choriocarcinoma, non-seminomatous germ cell testicular cancer, placental (trophoblastic tumor) and embryonal cancer, among others.

The term "H-hCG inhibitor or β-H-hCG inhibitor," as described above and used herein, refers to any agent, the application of which includes the inhibition of an H-hCG or H-hCG function or a H-hCG or β-H-hCG pathway function. "H-hCG or β-H-hCG function" as used herein should be construed to comprise the interaction of H-hCG or β-H-hCG with a cancer cell, the interaction of which produces an enhancement or spread of the cancer within the patient. Inhibition of function can be direct, such as in the case of an inhibitor that directly inhibits a required interaction by, for example, binding H-hCG or β-H-hCG or that directly inhibits the action or function of H-hCG or β-H-hCG by inhibiting the formation of H-hCG or β-H-hCG in cancer cells.

Inhibition of H-hCG or β-H-hCG function can also be indirect, such as inhibiting the synthesis or secondary modifications of H-hCG or β-H-hCG, such as precursors of H-hCG or β-H-hCG, including hCG or β-hCG or its mRNA, or inhibiting the pathway by which H-hCG or β-H-hCG elicits its effect. In mammalian cells, H-hCG or β-H-hCG can be regulated at the level of transcription by the anti-sense polynucleotides for hCG or β-hCG. By way of example, an H-hCG or β-H-hCG inhibitor can be an isolated nucleic acid, an antisense nucleic acid, an agent which inhibits the formation of a precursor molecule such as hCG or β-hCG, an agent which inhibits or effects glycosylation of hCG or β-hCG in cancer cells, including endoglycosidases, which cleave glycosides from H-hCG or β-H-hCG, which may be administered to the patient or expressed in a patient's cancer cells using methods well known in the art, an H-hCG or β-H-hCG-binding antibody or fragment thereof, other compounds or agents such as small molecules, polypeptides or fragments, thereof, which act to inhibit the effect of H-hCG or β-H-hCG on cancer cells. An inhibitor should not be construed to be limited to being derived only from the aforementioned classes of molecules. Methods for using or developing an inhibitor are described herein or are known to those skilled in the art. In addition, hCG or α- or β-hCG or peptide fragments thereof, preferably fragments of hCG of at least four contiguous amino acid units, alternatively, at least about 10 contiguous amino acid units, alternatively, at least about 15 contiguous amino acids, alternatively at least about 20 contiguous amino acids, at least about 30 contiguous amino acids, at least about 40 contiguous amino acids and at least about 50 contiguous amino acids may be used as competitive inhibitors of H-hCG and β-H-hCG, which are believed to act at least partially through the LH/hCG receptor in promoting cancer cell growth and/or metastasis.

It will be recognized by one of skill in the art that the various embodiments of the invention as described above relating to inhibitors of H-hCG and β-H-hCG may be used to inhibit the growth and/or the spread or metastasis of cancer in a patient, especially a human patient. In the case of a pregnant female or a female at risk to become pregnant, inhibitors of H-hCG and/or β-H-hCG, preferably antibodies, more preferably human or humanized monoclonal antibodies may be used to prevent pregnancy or to terminate an unwanted pregnancy.

Methods of Identifying Compounds Which Inhibit H-hCG and β-H-hCG Directly or Indirectly The invention includes a method of identifying compounds that can be used as anticancer agents or abortifacients by virtue of their direct or indirect impact on the action of H-hCG and β-H-hCG in cancer cells and tissue, or the direct impact of H-hCG and/or β-H-hCG on implantation of a fertilized ovum (pregnancy). This includes, but is not limited to, a method of identifying compounds which inhibit the formation of H-hCG and β-H-hCG in cancer cells. Another aspect of the invention includes more specifically, a method for identifying compounds which inhibit the formation of hCG or β-hCG, or the glycosylation of hCG or β-hCG. The method includes techniques for screening compounds which produce these effects. hCG, β-hCG, H-hCG and β-H-hCG can be measured using methods well known in the art. See, for example, Butler et al., *Brit. Journ. Cancer* 82(9): 1553-1556 (2000) and Lles, et al., *Prenatal Diagnosis* 19:790-792 (1999). In addition, the present invention may be used to determine inhibitors which act at the LH/hCG receptor and thus are potential anti-cancer agents. This is especially true of peptide fragments of hCG or α- or hCG, which may inhibit the action of H-hCG and β-H-hCG at the LH/hCG receptor on the cancer cell. Cell growth of cancer cells can be measured using various assays known to those skilled in the art. The invention also includes a method of identifying compounds which inhibit cancer growth and metastasis in animals. Preferably, the animal is a human.

The invention discloses herein methods for measuring H-hCG and β-H-hCG interactions with cancer cells, as well as various methods for measuring cancer cell growth and metastasis. In addition, methods for analyzing the results of the various types of assays in conjunction with one another are included to demonstrate the effect of an inhibitor of H-hCG and β-H-hCG on cancer cell growth.

In one aspect, the method used for screening inhibitors of H-hCG and β-H-hCG include assays to measure cancer cell growth. In another aspect, the method used for screening inhibitors of H-hCG and β-H-hCG include assays to measure the inhibition of hCG or β-hCG formation, precursors to H-hCG and β-H-hCG or the formation of H-hCG and/or β-H-hCG. Other assays measure the inhibition of potential anti-cancer agents such as hCG, β-hCG, fragments, thereof or other potential inhibitors which bind at the LH/hCG receptors or at TGFβ receptors and inhibit the binding of H-hCG and β-H-hCG. Assays utilizing LH/hCG receptors or TGFβ receptors on SWAN 6 cytotrophoblast cells, JAR choriocarcinoma, Jeg-3 choriocarcinoma cells, HKRT-11 testicular choriocarcinoma cells, NTERA testicular embryonal carcinoma cells, SCaBER or T24 bladder epithelial carcinoma cells, Hec-1-a Endometrial squamous cell carcinoma and KLE endometrial adenocarcinoma cells, among others, may be performed. Other studies may rely on classic receptor binding studies with isolated receptors, together with Millipore Multiscreen separator plate studies may be used.

In one embodiment, the method used for identifying inhibitors of H-hCG and β-H-hCG includes selecting receptors on cancer cells which stably bind to H-hCG and β-H-hCG as evidenced by specific binding assays. In alternative embodiments, the method used for identifying inhibitors of H-hCG and β-H-hCG includes selecting endometrial cells which stably bind to H-hCG and β-H-hCG as evidenced by binding assays. Once identified, inhibitors of the binding of H-hCG and β-H-hCG to these receptors may be identified as potential anti-cancer agents or as potential abortifacients for use in pregnancy prevention or termination.

In one aspect the identified inhibitor compounds include proteins and peptides and derivatives and fragments of hCG, β-hCG or TGFβ, thereof, in others, the identified compounds are small molecules, including peptidomimetics which mimic the binding of H-hCG and/or β-H-hCG at the LH/hCG or TGFβ receptor site and function as inhibitors or modulators of H-hCG and/or β-H-hCG binding.

In yet another aspect, the invention includes the identification of compounds, including, but not limited to, small molecules, drugs or other agents, for their ability to disrupt H-hCG and β-H-hCG binding or the formation of H-hCG and β-H-hCG by cancer cells (by inhibition of glycosylation reactions or the formation of hCG or β-hCG and H-hCG and/or β-H-hCG. For example, high throughput screens can be established to identify small molecules that inhibit H-hCG and β-H-hCG binding to LH/hCG or TGFβ receptors. Other high throughput screens can identify the amount of H-hCG and/or β-H-hCG produced, thus evidencing the relative inhibitory activity of a compound as an indirect inhibitor of H-hCG and/or β-H-hCG. The invention should not be construed to include the use of assays to identify only inhibitors of H-hCG and β-H-hCG interactions with LH/hCG or TGFβ receptor interaction, but should be construed to include assays to identify inhibitors of other H-hCG and β-H-hCG interactions as well.

In one embodiment, the compounds screened for their ability to inhibit H-hCG and β-H-hCG binding at LH/hCG receptors or TGFβ receptors include hCG, β-hCG, TGFβ and peptide fragments thereof as well as small molecules, including peptidomimetics which can inhibit the binding of H-hCG and β-H-hCG at these receptors by mimicking the binding aspects of H-hCG and/or β-H-hCG.

Assays for Testing Inhibitors of h-HCG and/or β-H-hCG Function and Interaction

The present disclosure establishes a series of assays for identifying inhibitors on H-hCG and/or β-H-hCG function and interactions and for inhibitors of cancer cell growth and metastasis and for compounds otherwise useful in the treatment of tumors and cancer. These assays can be then be used in conjunction with one another to identify and assay for the inhibitors which inhibit H-hCG and/or β-H-hCG dependent cell growth and/or metastasis. All of the cellular, biochemical and molecular assays described herein should be construed to be useful for the invention.

In one aspect, the invention discloses assays for measuring the effects of inhibitors on levels of hCG, β-hCG, H-hCG and/or β-H-hCG both in vivo and in vitro. These assays include sampling cells, conditioned media, tissues, and blood. In certain aspects of the invention, cells which produce measurable quantities of H-hCG and/or β-H-hCG are grown in the presence and absence of a potential inhibitor (direct or indirect) of the formation of H-hCG and/or β-H-hCG. Inhibitors are identified where the amount of H-hCG and/or β-H-hCG produced by the cells in the presence of potential inhibitor are reduced compared to cells grown in the absence of the potential inhibitor. A number of cell lines may be used for this assay aspect of the present invention including, for example, SWAN 6 cytotrophoblast cells, JAR choriocarcinoma, Jeg-3 choriocarcinoma cells, HKRT-11 testicular choriocarcinoma cells, NTERA testicular embryonal carcinoma cells, SCaBER or T24 bladder epithelial carcinoma cells, Hec-1-a Endometrial squamous cell carcinoma and KLE endometrial adenocarcinoma cells, among others.

In one embodiment hCG, β-hCG, H-hCG and/or β-H-hCG are measured by for example, carbohydrate analyses, immunoassays or combinations of these methods and may employ lectins that assay for the carbohydrate moieties, chromatography, chemical or electrophoresis or isoelectric focusing tests and/or antibodies to H-hCG and/or β-H-hCG. Included with these analyses are various techniques including immunoprecipitation and co-immunoprecipitation. These analyses may include, for example, far-western analyses. In yet another aspect of the invention ELISA assays can be used to measure hCG, β-hCG, H-hCG and/or β-H-hCG levels in the presence or absence of a candidate inhibitor. The invention also includes immunohistochemical and immunofluorescence assays to compare hCG, β-hCG, H-hCG and/or β-H-hCG levels in the presence or absence of a candidate inhibitor. Methods for identifying H-hCG and/or β-H-hCG may be found or adapted from the teachings of U.S. Pat. No. 6,429,018, relevant portions of which are incorporated by reference herein.

In another embodiment the function or activity of a potential inhibitor of H-hCG and/or β-H-hCG can be measured to identify the effects of candidate inhibitors on cancer cell growth and/or metastasis. The present invention provides for assays to measure function which include binding ability to LH/hCG and/or TGFβ receptors, inhibition of the formation and/or glycosylation of hCG and β-hCG, and the ability to enhance cancer cell growth and/or metastasis.

In another embodiment, assays and technique of the invention include molecular methods to identify inhibitors of H-hCG and/or β-H-hCG and to test the effects of candidate inhibitors on cancer cell growth. In one aspect the invention discloses methods to inhibit the interactions of H-hCG and/or β-H-hCG with cancer cells using antibodies and/or small molecules. In another aspect the invention can be used to inhibit H-hCG and/or β-H-hCG function using antisense techniques and transfection techniques.

The invention should not be construed to be limited solely to the assays described herein, but should be construed to include other assays as well. One of skill in the art will know that other assays are available to measure protein activity and function.

Assays for Testing Inhibitors of H-hCG and/or β-H-hCG By Measuring Cancer Cell Growth The invention also discloses methods for measuring cancer cell growth and/or metastasis in the present or absence of a potential H-hCG and/or β-H-hCG inhibitor. Inhibition of potential anti-cancer compounds may be assayed in cancer cell lines, which are well known in the art. For example, the following NCI panel may be utilized to assay the relative anti-cancer activity of a number of H-hCG and/or β-H-hCG inhibitors according to the present invention.

Testing of Compounds According to the Present Invention by NCI

The following cells lines are used to test the activity of compounds according to the present invention.

| Cell Line Name | Panel Name |
| --- | --- |
| CCRF-CEM | Leukemia |
| HL-60(TB) | Leukemia |
| K-562 | Leukemia |
| MOLT-4 | Leukemia |
| RPMI-8226 | Leukemia |
| SR | Leukemia |
| A549/ATCC | Non-Small Cell Lung Cancer |
| EKVX | Non-Small Cell Lung Cancer |
| HOP-18 | Non-Small Cell Lung Cancer |
| HOP-19 | Non-Small Cell Lung Cancer |
| HOP-62 | Non-Small Cell Lung Cancer |
| HOP-92 | Non-Small Cell Lung Cancer |
| NCI-H226 | Non-Small Cell Lung Cancer |
| NCI-H23 | Non-Small Cell Lung Cancer |
| NCI-H322M | Non-Small Cell Lung Cancer |
| NCI-H460 | Non-Small Cell Lung Cancer |
| NCI-H522 | Non-Small Cell Lung Cancer |
| LXFL 529 | Non-Small Cell Lung Cancer |
| DMS114 | Small Cell Lung Cancer |
| DMS 273 | Small Cell Lung Cancer |
| SHP-77 | Small Cell Lung Cancer |
| COLO 205 | Colon Cancer |

-continued

| Cell Line Name | Panel Name |
| --- | --- |
| DLD-1 | Colon Cancer |
| HCC-2998 | Colon Cancer |
| HCT-116 | Colon Cancer |
| HCT-15 | Colon Cancer |
| HT29 | Colon Cancer |
| KM12 | Colon Cancer |
| KM20L2 | Colon Cancer |
| SW-620 | Colon Cancer |
| SF-268 | CNS Cancer |
| SF-295 | CNS Cancer |
| SF-539 | CNS Cancer |
| SNB-19 | CNS Cancer |
| SNB-75 | CNS Cancer |
| SNB-78 | CNS Cancer |
| TE671 | CNS Cancer |
| U251 | CNS Cancer |
| XF 498 | CNS Cancer |
| LOX IMVI | Melanoma |
| MALME-3M | Melanoma |
| M14 | Melanoma |
| RPMI-7951 | Melanoma |
| M19-MEL | Melanoma |
| SK-MEL-2 | Melanoma |
| SK-MEL-28 | Melanoma |
| SK-MEL-5 | Melanoma |
| UACC-257 | Melanoma |
| UACC-62 | Melanoma |
| IGROV1 | Ovarian Cancer |
| OVCAR-3 | Ovarian Cancer |
| OVCAR-4 | Ovarian Cancer |
| OVCAR-5 | Ovarian Cancer |
| OVCAR-8 | Ovarian Cancer |
| SK-OV-3 | Ovarian Cancer |
| 786-0 | Renal Cancer |
| A498 | Renal Cancer |
| ACHN | Renal Cancer |
| CAKI-1 | Renal Cancer |
| RXF 393 | Renal Cancer |
| RXF-631 | Renal Cancer |
| SN12C | Renal Cancer |
| SN12K1 | Renal Cancer |
| TK-10 | Renal Cancer |
| UO-31 | Renal Cancer |
| P388 | Leukemia |
| P388/ADR | Leukemia |
| PC-3 | Prostate Cancer |
| DU-145 | Prostate Cancer |
| MCF7 | Breast Cancer |
| NCI/ADR-RES | Breast Cancer |
| MDA-MB-231/ATCC | Breast Cancer |
| HS 578T | Breast Cancer |
| MDA-MB-435 | Breast Cancer |
| MDA-N | Breast Cancer |
| BT-549 | Breast Cancer |
| T-47D | Breast Cancer |
| MAXF 401 | Breast Cancer |
| MDA-MB-468 | Breast Cancer |
| SK-BR-3 | Breast Cancer |

Results which show that the inhibitor exhibits enhanced activity against any one or more of the above mentioned cell lines, colon cancer cell lines, melanoma cell lines, renal cancer cell lines and a breast cancer cell line, thus showing the potential for broad activity of the inhibitors according to the present invention. Other cell lines which may be used to assess the anti-cancer of any one or more of inhibitors according to the present invention include, for example, choriocarcinoma, testicular choriocarcinoma, non-seminomatous germ cell testicular cancer, placental (trophoblastic tumor) and embryonal cancer cell lines.

Methods of Inhibiting or Treating Tumors/Cancer Disease Treatment of Cancer

Inhibitors of H-hCG and/or β-H-hCG may be used therapeutically to treat cancer in patients, especially human patients. A compound identified as an inhibitor of H-hCG and P—H-hCG, whether that inhibitor is a direct or indirect inhibitor of H-hCG and/or β-H-hCG can be administered to any patient in need of cancer treatment, including a human, in an effective amount to treat the cancer, by inhibiting the growth and/or metastasis of the cancer to be treated. The compound or known inhibitor may be administered via any suitable mode of administration, such as intramuscular, oral, subcutaneous, intradermal/transdermal, intravaginal, rectal, buccal, or intranasal administration, among others. The preferred modes of administration are oral, intravenous, subcutaneous, intramuscular or intradermal/transdermal administration. The most preferred mode is subcutaneous or oral administration, depending on the inhibitor utilized. The invention contemplates the use of an inhibitor of H-hCG and/or β-H-hCG to inhibit the growth and/or metastasis of cancer in animal patients. Preferably the patient is a human.

The present invention also relates to inhibiting or treating tumors and/or cancer in patients in need of such therapy. Some examples of diseases which may be treated according to the methods of the invention are described herein. These cancers include, but are not limited to, epithelial cancers, including carcinomas, malignant hematogenous, ascitic and solid tumors. Representative cancers which may be treated in the present invention include, for example, stomach, colon, rectal, liver, pancreatic, lung, breast, cervical, uterine, ovary, prostate, testis, bladder, renal, brain/CNS, head and neck, throat, Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' Tumor, neuroblastoma, hairy cell leukemia, mouth/pharynx, oesophagus, larynx, kidney, among others. The present invention may be used preferably to treat eutopic cancers such as choriocarcinoma, testicular choriocarcinoma, non-seminomatous germ cell testicular cancer, placental (trophoblastic tumor) and embryonal cancer, among others.

The invention should not be construed as being limited solely to the examples, as other tumors/cancers which are at present unknown, once known, may also be treatable using the methods of the invention. In one aspect the treated disease is cancer. A cancer may belong to any of a group of cancers which have been described, as well as any other viral related cancer.

The invention relates to the administration of an identified compound in a pharmaceutical composition to practice the methods of the invention, the composition comprising the compound or an appropriate derivative or fragment of the compound and a pharmaceutically acceptable carrier, additive or excipient. As used herein, the term "pharmaceutically acceptable carrier, additive or excipient" means a chemical composition with which an appropriate H-hCG and/or β-H-hCG inhibitor or derivative may be combined and which, following the combination, can be used to administer the appropriate inhibitor to an animal.

Pharmaceutical compositions according to the present invention may be administered to deliver a dose of between 1 ng/kg/day and 100 mg/kg/day to the patient in need of therapy.

The inhibitors which may be used in the present invention are generally formulated in the presence of a pharmaceutically acceptable carrier, additive or excipient. Pharmaceutically acceptable carriers, additives and excipients which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey). The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer, for example, peptides, fragments, or derivatives, and/or a nucleic acid encoding the same according to the methods of the invention. The method should not be construed to be limited to only peptides or fragments of H-hCG, β-H-hCG, hCG, β-hCG and TGFβ, but should be construed to include other proteins, peptides, fragments or derivatives thereof, as well as other types of molecules, agents, or compounds which exhibit inhibitory action, either directly or indirectly, on the action of H-hCG and/or β-H-hCG, to promote or enhance cancer cell growth and/or metastasis, or to prevent or reduce the likelihood of or terminate an unwanted pregnancy.

Compounds which are identified using any of the methods described herein may be formulated and administered to a mammal for treatment of various cancers described herein. In addition, direct inhibitors of H-hCG and β-H-hCG may be used to prevent or reduce the likelihood of a pregnancy or terminate an unwanted pregnancy.

The invention encompasses the preparation and use of pharmaceutical compositions comprising a compound useful for treatment of various cancers described herein or for preventing or reducing the likelihood of a pregnancy or terminating an unwanted pregnancy. Such a pharmaceutical composition may comprise the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise less than 0.1% to 100% (w/w) active ingredient.

In addition to the active ingredient, a pharmaceutical composition of the invention may further comprise one or more additional pharmaceutically active agents, including other anti-cancer agents. Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for a pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C. and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intrapentoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable fomulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) forin for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute about 0.1 to 20% (w/w) of the composition. The propellant may further comprise additional ingredients such as a liquid non-Ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as in ethylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nose.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (W/W) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "pharmaceutically acceptable additives" include, but are not limited to, one or more of the following: surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additives" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of cancer and disease state being treated, the age of the animal, the route of administration and the relative therapeutic index.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

As used herein, "alleviating a cancer disease symptom" means reducing the severity of the symptom.

As used herein, "treating tumors or cancer" means inhibiting the growth and/or spread of cancer or reducing the size of the tumor or number of cancer cells consistent with typical cancer treatment.

A "prophylactic" treatment is a treatment administered to a subject who does not exhibit signs of a disease or exhibits only early signs of the disease for the purpose of decreasing the risk of developing cancer. Typically prophylactic agents for use in the present invention exhibit a high therapeutical index and in particular, low toxicity.

A "therapeutic" treatment is a treatment administered to a subject who exhibits signs of cancer disease for the purpose of diminishing or eliminating those signs.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the seventy of a symptom of the disease or disorder, the frequency with which such a symptom is experienced by a patient, or both, are reduced.

Vaccines and Methods of Immunizing Patients Against Cancer and its Recurrence

Vaccines according to the present invention can be formulated and administered to immunize a patient against contracting a cancer or alternatively to prevent or reduce the likelihood that a patient whose cancer is in remission will suffer a relapse of cancer. These compositions may be formulated by any means that produces a contact of the active ingredient with the agent's site of action in the body of the patient to be treated. They can be administered by any conventional means available for use in conjunction with pharmaceutically acceptable carriers, additives and excipients. They can be administered alone, but are generally administered with a pharmaceutical carrier selected on the basis of the chosen route of administration and standard pharmaceutical practice.

Vaccines according to the present invention comprise H-hCG and/or β-H-hCG or immunogenic variant or fragment thereof in combination with a pharmaceutically acceptable carrier, excipient or additive, optionally in combination with an immunity enhancing effective amount of an adjuvant. Alternatively, the vaccine may comprise an expression vector which, when administered to a patient, expresses an immunogenic polypeptide in vivo, resulting in the continuous immunogenic response to the expressed immunogenic polypeptide. Such expression vectors express both hCG or β-hCG or a fragment thereof, as well as a glycolase enzyme which can glycosylate the expressed polypeptide to produce immunogenic forms of H-hCG and β-H-hCG, such as H-hCG and β-H-hCG, as well as immunogenic fragments or variants, thereof. The immunogen may be expressed as chimeric or fusion polypeptides with other immunogenic polypeptides or adjuvant polypeptides such as bovine serum albumin, human serum albumin, or fragments there of. Such expression vectors may be prepared pursuant to the teachings of U.S. Pat. Nos. 6,740,324 and 6,716,623, relevant portions of which are incorporated by reference herein, among other teachings well known by those of ordinary skill.

Fragments of H-hCG and/or β-H-hCG which may be used as immunogenic materials for use in vaccines include any fragment of H-hCG and/or β-H-hCG which elicits an immunogenic response in animals, preferably humans. Preferred fragments include at least an immunogenic portion of the carboxy-terminus of the β-subunit of H-hCG (see FIG. 1) and more preferably carboxy terminus polypeptides which are bonded to O-linked oligosaccharides, preferably comprising oligosaccharide O-linked amino acids 123-141 (the result of a tryptic digest of the β subunit, see FIG. 1) or other peptidase digest of the β-subunit. These fragments may be used alone in vaccines or in combination with other adjuvants or linked to other polypeptides as chimeric or fusion peptides, for example, other fragments of hCG or preferably adjuvant polypeptides such as bovine serum albumin (BSA) or human serum albumin (HSA), among other adjuvant polypeptides.

The active immunogen as a vaccine can be administered orally in solid dosage forms such as capsules, tablets and powders, or in liquid dosage forms such as elixirs, syrups, emulsions and suspensions. Preferably, the vaccine is formulated for administration parenterally by injection, rapid infusion, nasopharyngeal absorption or dermoabsorption. The agent may be administered intramuscularly, intravenously, or as a suppository. s In general, water, suitable oil, saline, aqueous dextrose (glucose), and related sugar solutions and glycols such as propylene glycol or polyethylene glycols are suitable carriers for parenteral solutions. Solutions for parenteral administration contain the immunogen optionally along with suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic.RTM.), a non-ionic surfactant, and a metabolizable oil such as squalene (U.S. Pat. No. 4,606,918).

In a method for immunizing a patient against cancer or the recurrence of cancer after remission, an immunogenic composition as a vaccine is administered to said patient to provide an immunogenic response to cancer. The vaccine may be administered in an initial effective dose, followed by booster doses, at intervals ranging from two months to 6 months or several years, depending upon the strength and duration of the patient's immunogenic response to the vaccine. Generally, the immunogenic peptide utilized will be obtained or derived from the same species as the patient. Preferably, the immunogenic polypeptide is a human H-hCG, β-H-hCG, or an immunogenic fragment or variant thereof when the patient is human.

It will be recognized by one of skill in the art that the various embodiments of the invention as described above relating to specific methods of treating tumors and cancer disease states may relate within context to the treatment of a wide number of other tumors and/or cancers not specifically mentioned herein. Thus, it should not be construed that embodiments described herein for the specific cancers mentioned do not apply to other cancers.

Kits for Inhibiting Cancer Cell Growth and/or Metastasis

The method of the invention includes a kit comprising an inhibitor identified in the invention and an instructional material which describes administering the inhibitor or a composition comprising the inhibitor to a cell or an animal. This should be construed to include other embodiments of kits that are known to those skilled in the art, such as a kit comprising a (preferably, sterile) solvent suitable for dissolving or suspending the composition of the invention prior to administering the compound to a cell or an animal. Preferably the animal is a human.

As used herein, an "Instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

In a cancer aspect of the present invention, inhibitors according to the present invention may be used alone or in combination with a second anti-cancer agent. For example, inhibitors of H-hCG and/or β-H-hCG may be co-administered with other traditional anti-cancer agents, for example, antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agents, such as gemcitabine and agents based upon campothecin and cis-platin.

The invention is described further in the following examples, which are illustrative and not limiting. All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

EXAMPLES

Materials and Methods

Serum and urine samples from early pregnancy and gestational trophoblastic diseases were accumulated at Yale University (pregnancy and gestational trophoblastic disease urine) under the control of the Internal Review Board, from 1997 to 1999, and at University of New Mexico under the control of the Internal Review Board (pregnancy and gestational trophoblastic disease serum), from 2002-2004. All serum samples were collected within one hour of phlebotomy and frozen at −80° C., and thawed for immunoassays. Serum was tested for total hCG and H-hCG.

Culture medium was collected from 90-100% confluent flasks of JAR and JEG-3 choriocarcinoma cell line, and NTERA testicular emrbyonal carcinoma cell line. Cell were cultured to confluency in RPMI-1640 medium with 10% fetal calf serum (RPMI-10%). Spent culture fluid was tested for total hCG and H-hCG.

Total hCG (all forms of hCG dimer and free β-subunit) was measured using the DPC Inc. (Los Angeles Calif.) Immulite hCG assay on the Immulite automated immunoassay platform. This assay is calibrated in mIU/ml against the 3rd International Standard. Values were converted to ng/ml using the previously published conversion factor (1, 15). This test has been shown to equally recognize, on a molar basis, regular hCG, nicked hCG, H-hCG, and free β-subunit (15). H-hCG was measured using the Nichols Institute Diagnostics Inc. (San Clamente Calif.), Invasive Trophoblast Antigen H-hCG test on the Nichols Advantage automated immunoassay platform (results in ng/ml).

Studies with monolayer cytotrophoblast cells were completed at Yale University in 1998. Purified cytotrophoblast cells in Dulbecco's High Glucose medium with 10% fetal calf serum (DHG-10%) were kindly provided by Harvey Kliman at Yale University. Cytotrophoblast cell were purified by Percoll density centrifugation from trypsin dispersed term pregnancy villous trophoblast tissue using the methods used by Harvey Kliman previously (27). Cytotrophoblast cells, prepared by the methods of Kliman, differentiate in culture. At time zero they are 100% cytotrophoblast cells (28). Theses cells continuously fuse, and by day 4 are mostly syncytiotrophoblast cells (28). Zero time cytotrophoblast cells were plated onto Matrigel membranes and control inserts (Biocoat Matrigel invasion membranes, BD Biosciences, Bedford, Mass. 01730), and cultured at 37° C. for 24 hours in DHG-10% culture fluid containing no additive, 10 ng/ml regular hCG (hCG batch CR127, kindly provided by Stephen Birken at Columbia University), or 10 ng/ml H-hCG (H-hCG batch C7 (7)), in triplicate. Matrigel membranes were processed and percentage invasion calculated as suggested by manufacturer in package inserts. Briefly, membranes are rehydrated in DHG-10% in the incubator for 2 hours before use. Membranes and control inserts are then plated (25,000 cells in 0.5 medium per plate). Plates are cultured for 24 hours, and membranes removed from inserts using a scalpel. Membranes are transferred to a slide using Cytoseal mounting medium (Stephens Scientific Inc., Riverdale N.J.), exposing the under surface and invaded cells. Cells are stained with DIF-Quich Stain (IMEB Inc., Chicago Ill.) to mark nuclei. Invaded cells are counted at 5 marked positions, at the center, and half way to the north, south, east and west extreme corners of the membranes. The 5 counts are averaged for each insert. Cell penetration of membranes or invasion is directly compared to that of correspondingly cultured control inserts and percentage invasion calculated using the formula provided by the manufacturer.

We investigated the effect of multiple concentrations of monoclonal antibody B152 (anti-H-hCG), on cultured cancer cell growth. JAR and JEG-3 choriocarcinoma cells, and NTERA testicular embryonal cancer cells (ATCC, Manassas Va.) were all seeded at 1000 cells per well in separate 96 well covered cell culture microtitre plates (Becton Dickinson, Meylan Cedex, France). Cell were cultures 24 hours in RPMI-10%. Each of the 3 lines of cells were then cultures a further 72 hours in RPMI-10% medium containing 0, 0.5, 2 and 10 µg/ml B152, in quadruplicate, and the same 4 concentrations of normal mouse IgG (Sigma Chemical Co., St Louis Mo.), as controls, in quadruplicate. Cultures were washed with phosphate-buffered saline, and cell density determined using our published microtitre plate tetrazolium blue method (29), a variation of the established tetrazolium dye cell culture methods of Twentyman and Luscome (30). Briefly, tetrazolium bromide (Sigma Chemnical, St Louis Mo.) was added in phosphate-buffered saline to each well and incubated for 3 hours. Solution were aspirated and replaced with dimethylsulfoxide (Sigma Chemicals), to dissolved the formed formizan crystals. The absorbance of each well was read at 570 mm in a microtitre plate reader. The action of antibody B152 on cell growth was determined from cell number following growth with B152 (in quadruplicate) relative to the average result for the 4 well treated with the corresponding concentration of mouse IgG. Values are mean±standard deviation (SD), percentages relative to zero B152/mouse IgG results. Student t-test test and Batholomew's test of increasing means were used to analyze results.

Transplantation of JEG-3 choriocarcinoma cells in to nude mouse was completed at University of New Mexico. All procedures were approved by the University of New Mexico Health Sciences Center, Animal Care and Use Committee. Six to eight week old athymic BALB/c, nu/nu nude mice were purchased from Charles River Laboratories (Wilmington Mass.), and hosted in the University of New Mexico Health Sciences Center Animal Care facility. JEG-3 cells were grown to to 70% confluence at in DHG-10% and harvested with trypsin and EDTA. Approximately 10 million cells were injected subcutaneously into each of the athymic mice. Mouse monoclonal antibody B152 was reconstituted in sterile PBS as 1 mg/ml and 0.3 ml was given through intraperitoneal injection. Normal mouse IgG was used as control. In the first study to test B152 effect on established tumors, B152 was given 2 weeks after subcutaneous transplantation, and continued twice a week for up to 2 weeks, or until the largest tumor reached 2 cm, the maximal tumor size set by the animal use protocol. In the second study to test the action of monoclonal antibody B152 on the tumor development, B152 was given at time of transplantation with the dose described above. The tumor cross-section area was measured before every treatment according to the formula: length×width× 3.14÷4. Student t-test was used to compare tumor sizes at the end of studies.

Results

We investigated the occurrence of H-hCG as a component of total hCG immunoreactivity (regular hCG+H-hCG+their respective free β-subunits) in serum and urine samples. As shown in Table 1, H-hCG accounts for 2±1% and 6±6% in serum, and for 0.8±0.3% in urine of total hCG immunoreactivity in benign cases of gestational trophoblastic disease (complete and partial hydatidiform mole, and quiescent gestational trophoblastic disease, respectively). In contrast, H-hCG accounts for 83±41% and 90±35% in serum, and for 84±24% in urine of total hCG immunoreactivity in cases with invasive trophoblastic and germ cell malignancies (choriocarcinoma and testicular germ cell malignancy). A very significant difference was observed between the proportion of total hCG immunoreactivity due to H-hCG in benign and invasive disease in serum samples P>0.00001 and urine samples P<0.0001.

As shown in Table 1, in FIG. 2, H-hCG accounts for the highest proportions of total hCG immunoreactivity at the time following implantation. In the $3^{rd}$, $4^{th}$, $5^{th}$ and $6^{th}$ complete weeks of gestation, H-hCG accounts for 50, 43, 31 and 23% of immunoreactivity in serum samples; in the $4^{th}$, $5^{th}$, $6^{th}$ and $7^{th}$ complete weeks for 72%, 54%, 23% and 9% of immunoreactivity in urine samples. A continuing decline is observed in urine samples (serum samples not available) through the remainder of pregnancy. A significant decline is found in serum samples between the $3^{rd}$ and $6^{th}$ complete week (P=0.004), and in urine samples between the $4^{th}$ and $7^{th}$ complete week (P<0.00005) and between the $7^{th}$ complete week and the third trimester of pregnancy (P=0.02).

hCG acts on an LH/hCG receptor on corpus luteal cells to promote progesterone production, through a cAMP-mediated pathway. We used cAMP measurements to assess LH/hCG biological activity at rat corpus luteal cells using purified normal midtrimester pregnancy urine hCG samples with low proportions of hyperglycosylated oligosaccharides, and purified choriocarcinoma urine hCG samples with high proportions of hyperglycosylated oligosaccharides (FIG. 3, Table 2). As shown, significantly lower biological activity was demonstrated by t test between choriocarcinoma preparations (H-hCG) and normal pregnancy hCG (regular hCG), P=0.02.

As shown in Table 1 (FIG. 2), H-hCG predominates in invasive states, whether choriocarcinoma, or very early pregnancy, in the week following implantation. Both states are primarily characterized by the presence of cytotrophoblast cells, the cells that produce H-hCG (15, 20, 23, 24). We considered a separate role for H-hCG in cytotrophoblast cell invasion. Dispersed cytotrophoblast cell were isolated from term placenta and cultured 24 hours on Matrigel membranes, either with no additive, with 10 ng/ml pure choriocarcinoma H-hCG (preparation C7 (7)), or 10 ng/ml pure pregnancy regular hCG (preparation P8 (7)). Cells penetrating inserts were counted and compared to control inserts. Invasion was calculated using the formula described by the manufacturer (FIG. 4, Table 3). H-hCG significantly increased invasion by cytotrophoblast cells (tTest, P=0.05). Regular hCG, decreased invasion (no significant difference). A significant difference was observed in the action of H-hCG and regular hCG (t test, β-0.025).

We considered the possibility that H-hCG acts upon cytotrophoblast cell growth. Monoclonal antibody B152 is specific for H-hCG (16). We used this monoclonal antibody to bind and block H-hCG action. JEG-3 choriocarcinoma cells were cultured to 70% estimated confluence in the absence of antibody. Cultures were washed and cells counted. Further flasks were cultures a further 24 hours with non-specific IgG (controls), or 24 hours in the presence of antibody B152. At this time cultures were washed and cells counted. As shown in Table 4, propagating cells 24 hours beyond 70% confluency led to a doubling in the number of cells. Propagating cells in the presence of monoclonal antibody B152 significantly limited further cell growth (1.3-fold increase versus 2-fold increase). A significant difference was observed by t test, in the number of cells after 24 hours of culture with and without B152, P=0.008.

Human choriocarcinoma cells rapidly form tumor when transplanted into athymic nude mice (26). We investigated the action of H-hCG in vitro using athymic nude mice with subcutaneously transplanted with JEG-3 cells (see FIG. 6). Subcutaneous tumors were clearly visible in mice after 2 weeks. At this time, mouse blood contained 1818±1842 ng/ml (±SD) H-hCG. Mice were then either treated twice weekly with intraperitoneal injections of B152 monoclonal anti-H-hCG or with a similar concentration of non-specific IgG (controls). As measured in the week and a half that followed tumors rapidly doubled in size in the control group. However, tumors ranged from −18% to +7%, or minimal changed while receiving monoclonal antibody B152. A significant difference was observed by t test between animals receiving and not receiving B152 at all growth points (2.5, 3 and 3.5 weeks) P=0.003. While a growth trend was observed in the control group ($r^2$=0.97), none was observed in those receiving B152 ($r^2$=0.15).

In a further experiment initial tumor formation or tumorigenesis was investigated in athymic nude mice newly transplanted with JEG-3 cells (see FIG. 7). Mice were either treated with twice weekly intraperitoneal injections of B152 monoclonal anti-H-hCG or with a similar concentration of non-specific IgG (controls). In the control group, tumor first appeared at 2 weeks and continued to grow to 4 weeks. Much smaller tumors, approximately one quarter of the size of the control group, formed in animals receiving monoclonal antibody B152. A significant difference was observed by t test between animals receiving and not receiving B152 at 2, 3 and 4 weeks, P=0.0071, 0.0031 and 0.012, respectively.

Discussion

The above described experiments examine the occurrences and biological functions of H-hCG. These studies confirm previous studies (14-19) showing that H-hCG accounts for a high proportion of hCG immunoreactivity in urine samples in early pregnancy, in the weeks following blastocyst implantation, and in choriocarcinoma cases. It also shows, for the first time, that H-hCG also accounts for a high proportion of hCG activity in serum samples in early pregnancy and choriocarcinoma, and in testicular germ cell carcinoma cases. These data clearly confirm a link between H-hCG and invasive tissues.

The results show that H-hCG, but not regular hCG, promotes growth and invasion by trophoblast cells, and that specific antibodies against H-hCG inhibit growth and invasion. Multiple cultures systems are investigated in vitro (isolated placenta cytotrophoblast cells and choriocarcinoma cell lines), and athymic nude mice transplanted with human choriocarcinoma cells in vivo. That monoclonal antibodies against H-hCG inhibit growth and invasion indicates that they are binding secreted H-hCG and suppressing it action.

The results of these experiments show six inter-related findings—

1. H-hCG is most abundant, accounting for the bulk of hCG-related molecules produced in invasive states, whether choriocarcinoma and testicular germ cell cancer (compared to molar pregnancy or quiescent gestational trophoblastic disease), or very early pregnancy in the $3^{rd}$ and $4^{th}$ weeks of gestation, those that follow implantation (compared to $5^{th}$ week of gestation until term).

2. H-hCG has significantly less biological activity at the rat corpus luteal LH/hCG receptor than regular hCG.

3. As published, H-hCG is produced by cytotrophoblast cells (14, 20), the invasive trophoblast cells (23, 24), whether of pregnancy or choriocarcinoma (15, 19, 20). Regular hCG is produced by different cells, differentiated syncytiotrophoblast cells (20). When cytotrophoblast cells are isolated from pregnancy placenta they invade Matrigel membrane inserts. H-hCG, but not regular hCG, significantly promoted invasion of cells through these membrane inserts.

4. Monoclonal antibody against H-hCG significantly inhibited growth of choriocarcinoma cells.

5. Human choriocarcinoma cells rapidly form tumor in vivo when transplanted into athymic nude mice. Monoclonal antibody against H-hCG significantly blocked initial tumor formation, and significantly limited existing human tumor growth in these nude mice.

6. Studies with cultured cytotrophoblast cells and choriocarcinoma cells in vitro, and in nude mice models, in vivo show that H-hCG is both produced by and acts upon the same cells.

A clear role for H-hCG in promoting both growth and invasion by pregnancy and choriocarcinoma cytotrophoblast cells, in vivo and in vitro. Since, monoclonal antibodies inhibit the H-hCG action in vivo and in vitro, it is inferred that H-hCG has to be secreted and then act upon a receptor on the same cells, or an autocrine mechanism. Considering that H-hCG is not optimal in promoting cAMP production at the corpus luteal LH/hCG receptor it possibly acts on a separate, or unknown receptor.

It is inferred that H-hCG clearly is a separate molecule to regular hCG. Regular hCG is optimal at the LH/hCG receptor (1, 9), while H-hCG is not. As shown here, H-hCG, but not regular hCG, promotes cytotrophoblast cell growth and invasion. This is a unique endocrine situation. We have 2 genes, one coding for the α-subunit and the other for the 1-subunit, both genes and resulting polypeptides form the common backbone of two independent molecules with separate functions, varying only in oligosaccharide structure. One molecule, regular hCG, is an endocrine, produced by syncytiotrophoblast cells and acting on he LH/hCG receptor on corpus luteal cells. The other molecule, H-hCG, is apparently an autocrine growth and invasion-promoting agent, produced and acting upon an unknown receptor on cytotrophoblast cells.

H-HCG is produced in early pregnancy at the time of implantation, by choriocarcinoma and testicular germ cells. A mouse monoclonal antibody against H-hCG effectively inhibited human choriocarcinoma tumor formation and tumor growth and development in athymic nude mice in vivo and in cultured cell in vitro. Human monoclonal antibodies with the same specificity, or appropriately modified mouse antibodies (humanized antibodies), or antagonists of H-hCG will likely be clinically useful in the specific cure of choriocarcinoma and testicular or other germ cell malignancies, or in the prevention of new tumor growth or recurring disease. Such antibodies or antagonists may also be potentially useful as a contraceptive in prevention of implantation. A human or humanized antibody is currently in preparation. Human clinical trials are being planned.

X-Ray crystallography studies with deglycosylated hCG shows that hCG 13-subunit is unique in having a cystine knot structure (27, 28). This rare structure comprises a specific arrangement of two contiguous disulfide bonds and the peptide chains linking them, penetrated and knotted by a third disulfide bond (27, 28). This cystine knot structure has only been found in hCG, transforming growth factor β (TGFβ) and several other cytokines (27, 28). Several authors, including Lei et al. (26), investigating H-hCG or other hCG-related molecules and trophoblast invasion mechanisms have suggested that the cystine knot structure may make the molecule like a cytokine, and explain its involvement in trophoblast invasion (26-28). Multiple studies have shown that TGFβ 1, -2 and -3 and their common receptors are all key elements along with their common receptors in trophoblast invasion or blastocyst implantation (29-51). Several studies have clearly shown invasion/implantation mechanisms involving interference in apoptosis, or interference in TGFβ-enhanced apoptosis, as enhancing cytotrophoblast proliferation (23, 34, 36, 43, 52, 47, 48, 53-58).

It seems more than a coincidence: firstly, that H-hCG as shown here and shown by Lei et al (26) is involved in trophoblast invasion; secondly, that H-hCG has this cystine knot structure like TGFβ; and thirdly, the abundance of research showing that TGFβ and other cytokines are key elements in trophoblast invasion, seemingly through modulation of apoptosis (29-32, 33-36, 48, 49, 37-47, 53-60). In support of this relationship, BeWo choriocarcinoma cells have been shown to produce H-hCG (15). As shown (36), when the TGFβ receptors on the surface of BeWo cells were isolated, a glycoprotein of molecular weight 38,000 (the size of H-hCG, 15) was bound to the receptor (36). Furthermore, it has also been shown that choriocarcinoma cells are invasive because of resistance to or blockage of the anti-invasion apoptosis actions of TGFβ-1 (33, 59, 60). We infer from our findings and all these numerous mechanistic studies (29-32, 33-36, 48, 49, 37-47, 53-60), that H-hCG, but not regular hCG, blocks or antagonizes TGFβ mediated apoptosis, by binding the TGFβ receptor, limiting the TGFβ induced anti-invasiveness/apoptosis.

The cystine knot structure is present in both regular hCG and H-hCG. We ask why would only H-hCG promote growth and invasion? As published (7), choriocarcinoma hCG (H-hCG), but not regular hCG, are uniquely cleaved between β-subunit Val 44 and Leu 45, hydrophobic sites that normally hydrogen bonds with the amino acids surrounding α78, an N-glycosylation site (7, 27, 28). We infer that the presence of a larger oligosaccharide at α78 limits hydrogen bonding to β-subunit Val 44 and Leu 45 or subunit interaction at this site. This makes the subunits more loosely associated on H-hCG, exposing β-subunit Val 44 and Leu 45 to cleavage. Consistent with this findings is the demonstration that the subunits of choriocarcinoma hCG dissociate much more rapidly than those of regular pregnancy hCG (61). We infer that the exposure of the β-subunit on H-hCG differentiates the action from that of regular hCG.

Further Examples

Invasive Activity of Choriocarcinoma Cell H-hCG on Matrigel Membranes and on Tumorigeneses and Tumor Growth in Nude Mice Models. Prevention of H-HCG-Initiated Invasion by Antibody B152.

In initial studies, isolated cytotrophoblast cells were prepared from term placenta according to the methods of Kliman et al, *Endocrinology* 118:1567-1582, 1986. Cells were then cultured 24 hours in triplicate on Matrigel membranes and control inserts. The cytotrophoblast cultures produced 2.3 ng/ml of H-hCG in a 24 hour period. Cell penetration of membranes were photographed and counted. Cell penetration was compared with that of control inserts. The percentage penetration or invasion was calculated using the formula described by the manufacturer. The experiment was repeated (triplicate 24 plate wells) with the addition of H-hCG, 10 ng/ml (C5H-hCG, from a choriocarcinoma patient). Matrigel invasion was calculated as 68% (vs. 40%), indicating that the additional H-hCG enhanced invasion 1.7-fold. Invasion experiments were also carried out with pure regular hCG lacking H-hCG (recombinant hCG dimer, produced in mouse cell line, purchased from Sigma). Matrigel invasion was calculated as 34%, indicating a reduction in invasion, and no enhancement whatsoever. Results were encouraging indicating that H-hCG, but not regular hCG, directly promotes invasion by cytotrophoblast cells.

We have now repeated similar experiments with JAR and JEG-3 choriocarcinoma cell lines. Trypsin-dispersed cells were centrifuged and taken up in Dulbecco's high glucose medium with 10% fetal calf serum and were plated onto Matrigel membranes and control inserts (5000 cells per membrane) in 24 well plates. JAR and JEG-3 cells (which both produce significant quantities of H-hCG) invaded Matrigel membranes over 24 hours. Invasion was examined with the addition of 0, 10 and 30 ng/ml H-hCG (preparation C5), and with the addition of H-hCG-free hCG to the membrane culture fluids. Each concentration was examined with 5 Matrigel and control membranes. The mean Matrigel invasion with 0 ng/ml H-hCG added was calculated as 65% and 48% (JAR and JEG-3). The mean Matrigel invasion was calculated at 81% and 83% (JAR), and 78% and 85% (JEG-3) with 10 and 30 ng/ml H-hCG added, respectively. A 1.47- and 1.51-fold promotion of invasion was observed at 10 and 30 ng/ml H-hCG respectively with JAR cells and 1.62- and 1.77-fold with JEG-3 cells. This indicated that that 10 ng/ml was close to maximal and that 30 ng/ml was superfluous. A statistical significance in cell invasion was observed demonstrated between 0 and 10 ng/ml, and between 0 and 30 ng/ml (P<0.05) with both cell lines. A small reduction in invasion was observed with both cell lines using H-hCG-free hCG, 30 ng/ml.

In further experiments, antibody B152 (monoclonal anti-H-hCG) was used to attempt to block Matrigel invasion by H-hCG-producing JAR cells and by H-hCG-producing testicular cancer (HKRT-11 cells). This experiment was carried with membranes each covered with medium containing 0, 10, 30 and 100 ng/ml B152 (5 membranes at each concentration). While at 0 ng/ml the mean Matrigel invasion was calculated as 62% and 48% respectively, at 0.1, 0.3 and 1.0 µg/ml B152 the mean Matrigel invasion was 40, 25 and 18% (JAR), and 37, 30 and 22% (HKRT-11) respectively. A significant trend was demonstrated using the number of cells invaded and Bartholomew's test for changing proportions (P<0.05).

Lei, et al., *Troph Res* 3:147-159, 1999 transfected JAR choriocarcinoma cells with cDNA to generate antisense hCGα mRNA, which blocked translation and production of hCG and thus H-HCG, a major variant of hCG (JAR antisense cells). These non-hCG producing JAR antisense cells almost completely lost their ability to invade Matrigel membranes, and lost their ability to generate tumors in the athymic BALB/c nu/nu nude mice (Lei, et al., *Troph Res* 3:147-159, 1999). As shown here, JAR choriocarcinoma cells actually produce H-HCG rather than regular hCG. As such, the conclusion of Lei and colleagues (Lei, et al., *Troph Res* 3:147-159, 1999), that regular hCG is critical to invasion, is erroneous. After conducting our own studies, what their work really shows in hindsight is that H-hCG is critical to invasion, confiming our observations.

Further Studies. Independent endometrial cancer research studies have been carried out, examining Hec50co endometrial cancer cells transplanted subcutis into athymic BALB/c nu/nu nude mice. Tumorigensis was observed (subcutaneous tumors formed), as was growth once tumor established (See, Dai, et al. Therapeutic mouse model for the treatment of advanced endometrial cancer. *AACR Special Conf Mouse Models of Cancer*, Lake Beuna Vista Fla., 2003 abstract.) In addition, choriocarcinoma cells were transplanted subcutis into athymic BALB/c nu/nu nude mice. After 2 weeks, clear subcutaneous tumors were formed in all mice, invading into muscle and organs below with extensive angiogenis. Tumor size was calculated as (length of tumor×width×π/4) Paraffin-imbedded slides were made and tumors examined. Non-villous trophoblast tissue identified, primarily cytotrophoblast cells, exactly like that on the periphery of a typical human choriocarcinoma nodule. Two experiments were carried out with nude mice. In the first experiment with 8 mice, after 2 weeks all had established tumors. The average H-hCG concentration (±SD) in mice blood at 2 weeks was high, 1818±1843 ng/ml vs. 24 ng/ml in JEG-3 cell cultures. These 2 week mice were either given intraperitoneal injections of control IgG, or of monoclonal antibody B152 (300 µg total, injections twice weekly). Tumor growth observed for 1.5 to 2 weeks (FIG. 8). Studies had to be stopped at this time because tumor exceeded 2 cm diameter, a tumor burden limit set by animal care protocol. Clearly B152 bound H-hCG limiting tumor growth. Using a t test a significant difference was noted between the B152-treated and the control mice at 3 (P=0.039) and 3.5 weeks (P=0.016). Choriocarcinoma tumor invaded rapidly with an extensive angiogenesis. This shows that B152, which blocks H-hCG, inhibited tumor progression (Dai and Cole, paper submitted).

In a further experiment, B152 (300 µg, twice weekly) or IgG were given as intraperitoneal injections to nude mice newly transplanted subcutis with JEG-3 choriocarcinoma cells (11 mice). As shown in FIG. 9, treatment with H-hCG limited tumorigensis. Tumor size measured 0, 14, 17 and 21 days after transplant. In the controls, tumor size (+SD) was 0, 79±58, 121±68 and 149±98 mm² at these 4 times. In the group receiving B152 the tumor size was 0, 13±7.6, 27±15, and 43±22 mm² at these 4 times. A significant difference was observed in result with B152-treated mice: t test at 14, 17 and 21 days, P=0.0071, P=0.0031 and P=0.012, respectively (Dai and Cole, paper submitted).

It is concluded from the experiments set forth above in our laboratory with Matrigel and from studies looking at nude mice models, that H-hCG promotes tumor invasion, and that H-hCG production is clearly critical to tumor progession and tumorigenesis. Also shown is that monoclonal antibody B152 binds H-hCG blocking or limiting its invasion/tumorigensis/tumor growth function. It is also concluded that while H-hCG has no, or minimal, LH-like activity, like regular hCG, it has a completely separate biologic function in making a cell invasive.

H-HCG Production by Cell Lines and Primary Cultures

To examine the scope of H-hCG or H-hCG-related immunoreactivity, hCG forms (H-hCG, free β-subunit and total hCG immunoreactivity) measured in the culture fluids of 24 hour 1$^{st}$ and 3$^{rd}$ trimester primary cultures of cytotrophoblast cells prepared according to the optimal procedures of Kliman et al. (Endocrinology 118:1567-1582, 1986; Cell Biol 1990; 87:3057-61). Culture fluids were also tested from SWAN6 8 week of pregnancy telomerase-immortalized cytotrophoblast cells, and from JAR, JEG-3 and BeWo choriocarcinoma cell lines, HKRT-11 testicular choriocarcinoma cell line, and NTERA-2 testicular embyonal cancer cell line, OVCA. All were cultured in Dulbecco's High Glucose—Ham's F12 medium, with 10% fetal calf serum. As shown in Table 5 of FIG. 10, all cultures produced H-hCG immunoreactivity. Some also produced H-hCG/hCG free β-subunit immunoreactivity.

H-hCG Production by Non-Invasive and Invasive Trophoblastic Disease, and in Patients with Choriocarcinoma Quiescent gestational trophoblast disease has been identified. In these cases, women produced low concentrations of hCG, in most cases <50 IU/L, for periods from <6 months to 16 years. During these periods only minimal changes were observed in the hCG results recorded at the multiple institution involved and at the USA hCG Reference Service. Dr. Cole and the USA hCG Reference Service have now identified, to date, over 90 such cases (Cole, et al., J. Reprod. Med., 47:433-444, 2002; Bloxam, et al. Placenta 18:93-108, 1997; and Khanlian, et al., Am J Obstet Gynecol, 188: 1254-1259, 2003). In all cases no tumor was visualized by MRI/CT/PT scans. In all cases, single agent or multi-agent chemotherapy did not appropriately abate the hCG result (Cole, et al., J. Reprod. Med., 47:433-444, 2002 Bloxam, et al. Placenta 18:93-108, 1997; and Khanlian, et al., Am J Obstet Gynecol, 188: 1254-1259, 2003). Other centers have observed similar cases (Kohorn, E. I., Gynecol Oncol 85:315-320, 2002 and Hancock and Tidy, Troph Dis Upd 4: 4-10, 2003). It is generally inferred that in these cases the hCG is coming from non-invasive syncytiotrophoblast cells. Laurence Cole and USA hCG Reference Service and other centers have now observed that in some cases (Cole, et al., J. Reprod. Med., 47:433-444, 2002; Kohorn, E. I., Gynecol Oncol 85:315-320, 2002 and Hancock and Tidy, Troph Dis Upd 4: 4-10, 2003; Khanlian, et al., Am J Obstet Gynecol, 188: 1254-1259, 2003 Cole, et al., Clin Obstet Gynecol, 46:533-540, 2003, that after a significant period of time with static disease (quiescent gestational trophoblast disease, quiescent GTD), cells can become transformed leading to invasive disease or choriocarcinoma. In these cases hCG levels abruptly increased, tumors were imaged and invasive disease identified. We have consulted in 7 such cases.

We measured total hCG and H-hCG in serum samples, and calculated the percentage of immunoreactivity due to H-hCG in 57 of these cases with non invasive trophoblastic disease (quiescent GTD), in 7 cases that after 1, 2, 3 and 4½ of quiescent GTD that developed invasive trophoblastic disease (PSTT, GTN or choriocarcinoma), and in 15 cases with proven invasive trophoblastic disease (GTN and choriocarcinoma), As shown in FIG. 11, H-hCG was <5% of total hCG concentration or not detected in 54 of 57 cases with non-invasive disease (quiescent GTD). In the remaining 3 cases H-hCG results were 9, 10 and 21% of total hCG. In contrast, H-hCG was >60% of total hCG in 7 of the 7 cases that developed invasive disease after a period with non-invasive disease. H-hCG results were equal to total hCG values (100% H-hCG) in 10 of 15 other cases with proven invasive disease. The remaining 5 cases had H-hCG concentration 32, 32, 39, 71, and 81% of total hCG concentration. This study indicates that H-hCG measurements completely distinguished invasive and non-invasive trophoblastic disease. Results indicate that using >30% H-hCG as a cut off, H-hCG was seemingly an absolute marker of invasive disease, or that H-hCG production may be directly associated with the presence of invasive cells.

H-HCGβ Binds a 70 kD Monomeric Binding Protein Like the TGFβ RII Receptor

Recent studies have shown that the hCG β-subunit produced by bladder and cervical cancer cells promotes growth and invasion (Butler, et al., British Journal of Cancer. 82(9): 1553-1556, 2000; Butler, et al., Journal of Molecular Endocrinology. 22: 185-192, 1999; and Gillott, et al., *Br. J. Cancer* G73. 323-326, 1996). Our laboratory and others have shown that cervical cancer cell lines and other non-trophoblastic cancer cell lines produce a larger free β-subunit than that produced in pregnancy (Cole and Hussa, *Endocrinology*, 109: 2276-2279, 1981 and Hussa, et al., *Canc Res.* 46:1948-54, 1986). Recently, we have recognized that the larger size matched that of H-hCG β-subunit, and that the large size could be abated with endoglycosidases which remove sugar size chains. After endoglycosidase treatment the size in the same as H-hCG demonstrating that the larger size is due to hyperglycosylation so that the free β subunit produced by these cell lines is H-hCG free B subunit. It is thus concluded that it is H-hCG β-subunit which promotes growth and invasion in cervical and bladder cancer cells.

Radiolabeled H-hCG β (from bladder cancer cells cultured with $S^{32}$-labeled Methionine) binds to a specific protein or receptor on the surface of bladder cancer cells. Binding is specific in that it can be competed out by co-incubation with excess unlabeled H-hCG. β-subunit affinity chromatography was used to separate a membrane preparation from cultured bladder carcinoma cells. H-hCGβ-subunit binding protein was isolated. SDS-PAGE analysis identified a single 70 kD protein (FIG. 12). Denaturation did not change the migration or intensity of the protein on SDS-PAGE indicating that the β-subunit binding protein is a monomer. The size of this H-hCG β-subunit binding protein, and its presence as a monomer, is identical to that of the TGFβ RII receptor subunit.

H-hCGβ Reverses TGFβ Induced Apoptosis in Bladder Carcinoma Cells

Epithelial bladder carcinoma cells (T24 and 5637) were cultured in 96 well plates can be forced into apoptosis by incubation with TGFβ. However when these cells are co-incubated with increasing concentrations of H-hCGβ the apoptosis is reduced. At the same molar concentration H-hCGβ was found to completely reverse the apoptotic effect of TGFβ. Apoptosis is estimated using quantification of nucleosomes released into the culture medium during the apoptotic cascade. This data is then expressed as percentage change in nucleosome concentration and is proportional to apoptosis. As shown in FIG. 13, a sharp rise was observed in the percentage nucleosome concentration, hence an increase in apoptosis was found following the initial incubation with 100 pmol/ml TGFβ1. The effect gradually diminishes to below 100% (zero control) as the concentration of H-hCGβ increased from 0 to 400 pmol/ml, despite the continued presence of TGFβ. This shows that H-hCGβ inhibits apoptosis in these 2 cell lines, in a mechanism involving blocking the TGFβ3 receptor.

Inhibition of the Growth of Cancer Cells in Vitro

In this group of experiments, cancer cells were cultured in RPMI 10% fetal calf serum culture fluid in quadruplicate, 1000 cells per dish, for 24 hours, in 96 well plates. At the end of the aforementioned 24 hour period, numerous cells had solidly adhered to plates. The cells were then cultured in quadruplicate with media containing 0, 0.5, 2 and 10 micrograms per ml of B152 mouse monoclonal antibody (binds to H-hCG), or alternatively, in quadruplicates with 0, 0.5, 2 and 10 micrograms per ml of mouse non-specific IgG (no binding to H-hCG), as controls. After allowing the cells to grow in culture for a further 72 hours, medium was removed from each well, and the cells washed. At this time the number of cells was estimated using the very well established tetrazolium salt (MTT) method. The method measures membrane proteins, with the total amount of proteins proportional to the total amount of cells. Upon incubation, a blue color is formed. This color is accurately measured in a 96 well microtiter plate reader.

The number of cells for each category described above is determined from the absorbance reading at 570 nm representing the number of cells, minus controls. The results for the cells incubated with the 4 concentrations of B152 are expressed as a percentage of the control results for the corresponding cultures incubated with non-specific IgG. Each of the results for the 4 cultures treated with 10 micrograms per ml B152, for example, is divided by the average result for the 4 control cultures treated with 10 microgram/ml IgG). The mean result (%) is determined as is the standard deviation.

The identical procedures described above were performed with 7 cell lines, each incubated in RPMI 10% fetal calf serum culture fluid. The cell lines were JAR choriocarcinoma cells, JEG3 choriocarcinoma cells, NTERA testicular emryonal carcinoma cells, SCABER bladder epithelial carcinoma cells, T24 bladder epithelial carcinoma cells, HEC1A endometrial squamous cell carcinoma, KLE endometrial adenocarcinoma cells. All were purchased from ATCC, Rockville, Md. or Manassas, Va., USA.

Table 6, below, clearly shows, that when cancer cells are cultured with increasing concentrations of monoclonal antibody B152 (against H-hCG) the cells are increasing inhibited from growing. All values are expressed as a percentage of cell growth compare to the effect of an equivalent concentration of non-specific mouse antibody. In HEC1A Endometrial cancer cells, for instance, when cells are grown with 0.5 μg/ml B152 the cell growth is 91%±4.8% of that with no added antibody, when cultured with 2 μg/ml B152 the cell growth is only 78%±3.3% of that with no added antibody, and when culture with 10 μg/ml B152 the cell growth is only 74%±7.0 of that with no added antibody. Very clearly, as the concentration of B152 is increased in the culture fluid (vs. equivalent concentration of non-specific mouse antibody) cancer cell growth is inhibited.

TABLE 6

| Cell Line | 0 µg/ml B152:IgG (%) Mean ± SD | 0.5 µg/ml B152:IgG (%) Mean ± SD | 2 µg/ml B152:IgG (%) Mean ± SD | 10 µg/ml B152:IgG (%) Mean ± SD |
|---|---|---|---|---|
| JAR Choriocarinoma Cells[a] | 100% ± 11% | 86% ± 1.3% | 73% ± 7.3% | 68 ± 8.2 |
| JEG3 Choriocarcinoma Cells[b] | 100 ± 7% | 103% ± 7.0% | 93% ± 3.0% | 83% ± 5.1 |
| NTERA Testicular Embryonal Carcinoma[c] | 100% ± 19% | 37% ± 3.4% | 33% ± 1.6% | 32% ± 6.2 |
| SCABER Bladder Epithelial Carcinoma[d] | 100% ± 2.0% | 102% ± 14.0% | 89% ± 9.1% | 86% ± 4.4 |
| T24 Bladder Epithelial Carcinoma Cells[e] | 100% ± 4.4% | 88% | 86% ± 1.7% | 84% ± 4.1 |
| HEC1A Endometrial Squamous Cell Carcinoma[f] | 100% ± 0.4% | 91% ± 4.8% | 78% ± 3.3% | 74% ± 7.0 |
| KLE Endometrial Adenocarinoma Cells[g] | 100% ± 10% | 68% ± 2.4% | 60% ± 3.7% | 57% ± 3.5% |

[a]A significant decrease observed in means for % cell growth (Batholomew's test), P = 0.001, and a significant difference observed between 0 and 2 µg/ml B152 (P = 0.006), and 0 and 10 µg/ml (P = 0.02).
[b]A significant decrease observed in means for % cell growth (Batholomew's test), P = 0.002, and a significant difference observed between 0 and 10 µg/ml B152 (P = 0.02).
[c]A significant decrease observed in means for % cell growth (Batholomew's test), P < 0.0005, and a significant difference observed between 0 and 0.5 µg/ml B152 (P = 0.006), 0 and 2 µg/ml (P = 0.009) and 0 and 10 µg/ml (P = 0.009).
[d]A significant decrease observed in means for % cell growth (Batholomew's test), P = 0.033, and a significant difference observed between 0 and 10 µg/ml (P = 0.004).
[e]A significant decrease observed in means for % cell growth (Batholomew's test), P < 0.0005, and a significant difference observed between 0 and 2 µg/ml B152 (P = 0.004), and 0 and 10 µg/ml (P = 0.003).
[f]A significant decrease observed in means for % cell growth (Batholomew's test), P < 0.0005, and a significant difference observed between 0 and 0.5 µg/ml B152 (P = 0.03), 0 and 2 µg/ml (P = 0.0001) and 0 and 10 µg/ml (P = 0.002).
[g]A significant decrease observed in means for % cell growth (Batholomew's test), P < 0.0005, and a significant difference observed between 0 and 0.5 µg/ml B152 (P = 0.006), 0 and 2 µg/ml (P = 0.0002) and 0 and 10 µg/ml (P = 0.004).

This table (also depicted in FIG. 14) shows that just as B152 inhibits the growth of choriocarcinoma cells, it similarly inhibits the growth of testicular cancer, endometrial cancer and bladder cancer cells. Based upon these results, it is expected that it will inhibit the growth of most cancer cells in this same way.

REFERENCES

1. Cole L A. Immunoassay of human chorionic gonadotropin, its free subunits, and metabolites. Clin Chem 1997; 43:2233-43.

2. Cole L A, Kardana A. Discordant results in human chorionic gonadotropin assays. Clin Chem 1992; 38:263-70.

3. Cole L A, Hussa R O. The carbohydrate on human chorionic gonadotropin produced by cancer cells. Adv Exp Med Biol 1984; 176:245-70.

4. Cole L A. O-Glycosylation of proteins in the normal and neoplastic trophoblast. Troph Res 1987; 2:139-48.

5. Cole L A. The O-linked oligosaccharides are strikingly different on pregnancy and choriocarcinoma hCG. J Clin Endocrinol Metab 1987; 65:811-13.

6. Amano J, Nishimura R, Mochizuki M, Kobata A. Comparative study of the mucin-type sugar chains of human chorionic gonadotropin present in the urine of patients with trophoblastic diseases and healthy pregnant women. J Biol Chem 1988; 263:1157-65.

7. Elliott M M, Kardana A, Lustbader J W, Cole L A. Carbohydrate and peptide structure of the α- and β-subunits of human chorionic gonadotropin from normal and aberrant pregnancy and choriocarcinoma. Endocrine 1997; 7:15-32.

8. Takamatsu S, Oguri S, Toba Minowa M, Yoshida A, Nakamura K, Takeuchi M, Kobata A. Unusually High Expression of N-Acetylglucosaminyltransferase-IVa in Human Choriocarcinoma Cell Lines: A Possible Enzymatic Basis of the Formation of Abnormal Biantennary Sugar Chain Cancer Res 1999; 59:3949-3953.

9. Kobata A, Takeuchi M. Structure, pathology and function of the N-linked sugar chains of human chorionic gonadotropin. Biochim Biophys Acta. 1999; 1455:315-26

10. Peters B P, Krzesicki R F, Hartle R J, Perini F, Ruddon R W A kinetic comparison of the processing and secretion of the alpha beta dimer and the uncombined alpha and beta subunits of chorionic gonadotropin synthesized by human choriocarcinoma cells. J Biol. Chem. 1984; 259:15123-30.

11. Hussa R O. Immunologic and physical characterization of human chorionic gonadotropin and its subunits in cultures of human malignant trophoblast. J Clin Endocrinol Metab 1977; 44: 1154-62.

12. Mann K, Karl H J. Molecular heterogeneity of human chorionic gonadotropin and its subunits in testicular cancer. Cancer 1983; 52:654-60.

13. Imamura S. Armstrong G A, Birken S, Cole L A, Canfield R E. Detection of desialylated forms of human chorionic gonadotropin. Clin Chim Acta 1987; 163:339-49.

14. Cole L A, Shahabi S, Oz U A, Bahado-Singh R O, Mahoney M J. Hyperglycosylated human chorionic gonadotropin (invasive trophoblast antigen) immunoassay: A new basis for gestational Down syndrome screening. Clin Chem 1999; 45:2109-19.

15. Cole L A, Khanlian S A, Sutton J M, Davies S, Stephens N. H-hCG (Invasive Trophoblast Antigen, H-HCG) a Key Antigen for Early Pregnancy Detection. Clin Biochem, 2003; 36:647-655

16. Birken S, Krichevsky A, O'Connor J, Schlatterer J, Cole L A, Kardana A, Canfield R. Development and characterization of antibodies to a nicked and hyperglycosylated form of hCG from a choriocarcinoma patient: generation of antibodies that differentiate between pregnancy hCG and choriocarcinoma hCG. *Endocrine* 1999; 10:137-44.

17. O'Connor J F, Ellish N, Kakuma T, Schlatterer J, Kovalevskaya G. Differential urinary gonadotrophin profiles in early pregnancy and early pregnancy loss. *Prenat Diagn* 1998; 18:1232-40.

18. Kovalesvskaya G, Birken S, Kakuma, Kakuma T, Ozaki N, Sauer M, Lindheim S, Cohen M, Kelly A, Sclatterer J, O'Connor J. Differential expression of human chorionic gonadotropin (hCG) glycosylation isoforms in failing and continuing pregnancies: preliminary characterization of the H-hCG isotope. *J Endocrinol* 2002; 172:497-506.

19. Kovalesvskaya G, Birken S, Kakuma T, O'Connor J F. Early pregnancy human chorionic gonadotropin (hCG) isoforms measured by immunometric assay for choriocarcinoma-like hCG. *J Endocrinol* 1999; 161:99-106.

20. Kovaleskaya G, Genbacev O, Fisher S J, Caceres E, O'Connor J F. Trophoblast origin of hCG isoforms: cytotrophoblasts are the primary source or choriocarcinoma-like hCG. *Mol Cell Endocrinol* 2002; 94:147-55.

21. Butler S A, Khanlian S A, Cole L A. Detection of early pregnancy forms of human chorionic gonadotropin by home pregnancy test devices. *Clin Chem* 2001; 47:2131-06.

22. Cole L A, Khanlian S A, Sutton J M, Davies S, Rayburn W F. Accuracy of home pregnancy tests at the time of missed menses. *Am J Obstet Gynecol* 2004; 190: 100-05.

23. Genbacev O. DiFederico E. McMaster M. Fisher S J. Invasive cytotrophoblast apoptosis in pre-eclampsia. *Human Reproduction.* 1999; 2:59-66.

24. Tarrade A. Goffin F. Munaut C. Lai-Kuen R. Tricottet V. Foidart J M. Vidaud M. Frankenne F. Evain-Brion D. Effect of matrigel on human extravillous trophoblasts differentiation: modulation of protease pattern gene expression. *Biology of Reproduction.* 2002; 67:1628-37

25. Cole, L. A. O-Glycosylation of proteins in the normal and neoplastic trophoblast. *Troph. Res.,* 1987; 2139-1487.

26. Lei Z M, Taylor D D, Gercel-Taylor C, Rao C V. Human chorionic gonadotropin promotes tumorigenesis of choriocarcinoma JAR cells. *Troph Res* 1999; 13:147-59.

27. Lapthorn, A. J., Harris, D. C., Littlejohn, A., Lussbader, J. W., Canfield, R. E., Machin, K. J., Morgan, F. J., Isaacs, N. W., Crystal structure of hCG. *Nature* 369: 455-461, 1994.

28. Wu H, Lustbader J W, Liu Y, Canfield R E, Hendrickson W A. Structure of hCG at 2.6A resolution from MAD analysis and selenomethionyl protein. *Structure* 1994; 2:545-8.

29. Lala P. K., Graham, C. H. Mechanisms of trophoblast invasiveness and their control: the role of proteases and protease inhibitors. *Cancer Metast Rev* 9: 369-379, 1990.

30. Strickland, S., Richards, W. G., Invasion of the Trophoblasts. *Cell* 71:355-357, 1992.

31. Lash, G. E., Cartwright, J. E., Whitley, G. S., Trew, A. J., Baker, P. N. The effects of angiogenic growth factors on extravillous trophoblast invasion and motility. *Placenta* 20(8): 661-7, 1999.

32. Caniggia, I., Grisaru-Gravnosky, S., Kuliszewsky, M., Post, M., Lye, S. J., Inhibition of TGF-B3 restores the invasive capability of extravillous trophoblasts in preeclamptic pregnancies. *J Clin Invest* 103:1641-1650, 1999

33. Khoo, N. K., Bechberger, J. F., Shepherd T, Bond, S. L., McCrae, K. R., Hamilton, G. S., Lala, P. K. SV40 Tag transformation of the normal invasive trophoblast results in a premalignant phenotype. I. Mechanisms responsible for hyperinvasiveness and resistance to anti-invasive action of TGFβ. *Intl J Cancer,* 77:429-39, 1998.

34. Graham, C. H., Lysiak, J. J., McCrae, K. R., Lala P. K. Localisation of transforming growth factor-beta at the human fetal-maternal interface: role in trophoblast growth and differentiation. *Biol Reprod,* 46:561-572, 1992.

35. Lala P. K., Hamilton, G. S. Growth factors proteases and protease inhibitors in the maternal-fetal dialogue. *Placenta,* 17: 545-555, 1996.

36. Mitchell E J, Lee K, O'Conner-McCourt M D. Characterization TGF-β receptors on BeWo choriocarcinoma cells including the identification of a novel 38-kDa TGF-beta binding blycoprotein. *Mol Biol Cell* 3:1295-307, 1992

37. Chen J. Laughlin L S. Hendrickx A G. Natarajan K. Lasley B L. The effect of 2,3,7,8-tetrachlorodibenzo-p-dioxin (TCDD) on chorionic gonadotrophin activity in pregnant macaques. *Toxicol* 186:21-31, 2003

38. Makrigiannakis A. Zoumakis E. Kalantaridou S. Margioris A. Chrousos G P. Gravanis A. Corticotropin-releasing hormone (CRH) and immunotolerance of the fetus. *Biochemical Pharmacol* 65:917-21, 2003

39. Aschkenazi S. Straszewski S. Verwer K M. Foellmer H. Rutherford T. Mor G. Differential regulation and function of the Fas/Fas ligand system in human trophoblast cells. *Biol Reprod* 66(6):1853-61, 2002

40. Leach R E. Romero R. Kim Y M. Kilburn B. Das S K. Dey S K. Johnson A. Qureshi F. Jacques S. Armant D R. Pre-eclampsia and expression of heparin-binding EGF-like growth factor. *Lancet.* 360:1215-9, 2002

41. Kauma S, Matt D, Strom S, Eierman D and Turner R. Interleukin-1, human leukocyte antigen HLA-DR and transforming growth factor-β expression in endometrium, placenta and placental membranes. *American Journal of Obstetrics and Gynaecology* 163:1430-1437, 1990.

42. Kayisli U A. Mahutte N G. Arici A. Uterine chemokines in reproductive physiology and pathology. *Am J Reprod Immunol* 47:213-21, 2002

43. Hung T H. Skepper J N. Burton G J. Hypoxia-reoxygenation: a potent inducer of apoptotic changes in the human placenta and possible etiological factor in preeclampsia. *Circulation Res* 90:1274-81, 2002

44. Zhou Y. McMaster M. Woo K. Perry J. Damsky C. Fisher S J. Vascular endothelial growth factor ligands and receptors that regulate human cytotrophoblast survival are dysregulated in severe preeclampsia and hemolysis, elevated liver enzymes, and low platelets syndrome. *Am J Path* 160 (4):1405-23, 2002

45. Emmer P M. Steegers E A. Kerstens H M. Bulten J. Nelen W L. Boer K. Joosten I. Altered phenotype of HLA-G expressing trophoblast and decidual natural killer cells in pathological pregnancies. *Human Reprod* 17:1072-80, 2002

46. Selam B. Kayisli U A. Mulayim N. Arici A. Regulation of Fas ligand expression by estradiol and progesterone in human endometrium. *Biol Reprod.* 65(4):979-85, 2001

47. Mor G. Gutierrez L S. Eliza M. Kahyaoglu F. Arici A. Fas-fas ligand system-induced apoptosis in human placenta and gestational trophoblastic disease. *Am J Reprod Immunol* 40:89-94, 1998

48. Simpson, H., Robson, S. C., Bulmer, J. N., Barbe,r A, Lyall, F. Transforming growth factor-β Expression in human placenta and placental bed during early pregnancy. *Placenta,* 23: 44-58, 2002.

49. Lysiak J J, Hunt J, Pringle G A, Lala P K. Localization of TGFβ and its natural inhibitor decorin in the human placenta and deciduas throughout gestation. *Placenta* 16:221-31, 1995.

50. Selick C E, Horowitz G M, Gratch M, Scott R T Jr, Navot D, Hofmann G E. Immunohistochemical localization 50. of transforming growth factor-beta in human implantation sites. *J Clin Endocr Metab* 1994:78:592-6.

51. Vuckovic M, Genbacev O, Kumar S. Immunohistochemical localisation of transforming growth factor-beta in first and third trimester human placenta. *Pathobiology* 60:149-51, 1992.

52. Fei G. Peng W. Xin-Lei C. Zhao-Yuan H. Yi-Xun L. Apoptosis occurs in implantation site of the rhesus monkey during early stage of pregnancy. *Contraception.* 64:193-200, 2001

53. Neale D. Demasio K. Illuzi J. Chaiworapongsa T. Romero R. Mor G. Maternal serum of women with pre-eclampsia reduces trophoblast cell viability: evidence for an increased sensitivity to Fas-mediated apoptosis. *J Matern Fetal Neonat Med.* 13(1):39-44, 2003 Jan.

54. Aschkenazi S. Straszewski S. Verwer K M. Foellmer H. Rutherford T. Mor G. Differential regulation and function of the Fas/Fas ligand system in human trophoblast cells. *Biol Reprod* 66:1853-61

55. Kamsteeg M. Rutherford T. Sapi E. Hanczaruk B. Shahabi S. Flick M. Brown D. Mor G. Phenoxodiol—an isoflavone analog—induces apoptosis in chemoresistant ovarian cancer cells. *Oncogene.* 22:2611-20, 2003

56. Neale D. Iluzi J. Romero R. Mor G. Maternal serum of women with pre-eclampsia reduces trophoblast cell viability: evidence for an increased sensitivity to Fas-mediated apoptosis. *J Mat-Fetal & Neonat Med.* 13:3944

57. Mor G. Straszewski S. Kamsteeg M. Role of the Fas/Fas ligand system in female reproductive organs: survival and apoptosis. *Biochem Pharmacol* 64:1305-15, 2002

58. Song J. Rutherford T. Naftolin F. Brown S. Mor G. Hormonal regulation of apoptosis and the Fas and Fas ligand system in human endometrial cells. *Molec Human Reprod* 8:447-55, 2002

59. Xu G, Chakraborty C, Lala P. K. Restoration of TGF-β regulation of plasminogen activator inhibitor-1 in Smad3—restituted human choriocarcinoma cells. *Biochem Biophys Res Comm,* 294: 1079-1086, 2002.

60. Graham, C. H., Connelly, I., MacDougall, J. R., Kerbel R. S., Stetler-Stevenson, W. G., Lala, P. K. Resistance of malignant trophoblast cells to both the anti-proliferative and anti-invasive effects of transforming growth factor-β. *Exper Cell Res,* 214:93-99, 1994.

61. Butler, S. A., Cole, L. A., Chard, T., and Iles, R. K. Dissociation of hCG into its free subunits is dependent on naturally occurring molecular structural variation, sample matrix and storage conditions. *Ann Clin Biochem,* 35:754-760, 1998.

62. Dai D, Laidler L L, Nguyen T, Al-BH-hCGr L, Leslie K K. Therapeutic mouse model for the treatment of advanced endometrial cancer. *AACR Special Conf Mouse Models of Cancer, Lake Beuna Vista Fla.,* 2003 abstract.

---

I claim:

1. A method of inhibiting the growth or metastasis of choriocarcinoma, testicular choriocarcinoma or non-seminomatous germ cell testicular cancer in a patient in need thereof comprising exposing cancer cells or tissue in said patient to an effective amount of an antibody which binds specifically to and inhibits the biological response of hyperglycosylated human chorionic gonadotropin (H-hCG) or beta-hyperglycosylated human chorionic gonadotropin (β-H-hCG), without appreciably binding to hCG or β-hCG.

2. The method according to claim 1 wherein said antibody binds specifically to H-hCG.

3. The method according to claim 1 wherein said antibody is a humanized monoclonal antibody.

4. The method according to claim 1 wherein said cancer is choriocarcinoma, and said antibody is a monoclonal antibody that binds to H-hCG.

5. The method according to claim 1 wherein said cancer is choriocarcinoma or testicular choriocarcinoma and said antibody is a monoclonal antibody that binds to H-hCG.

6. The method according to claim 1 wherein said antibody is an antagonist of H-hCG or β-H-hCG binding to cancer cells.

7. The method according to claim 1 wherein said patient is human.

8. The method according to claim 2 wherein said patient is human.

9. The method according to claim 3 wherein said patient is human.

10. The method according to claim 6 wherein said patient is human.

11. The method according to claim 4 wherein said patient is human.

12. The method according to claim 5 wherein said patient is human.

* * * * *

SEQUENCE LISTING

```
<160> NUMBER OF SEQ ID NOS: 2

<210> SEQ ID NO 1
<211> LENGTH: 92
<212> TYPE: PRT
<213> ORGANISM: Homo sapiens
<220> FEATURE:
<221> NAME/KEY: CARBOHYD
<222> LOCATION: (1)..(92)
<223> OTHER INFORMATION: Sites of N-glycosylation at residues 52 and 78.
      Sites of potential nicking of internal peptide bonds after
      residues 1, 2, 3 and 42.

<400> SEQUENCE: 1

Ala Pro Asp Val Gln Asp Cys Pro Glu Cys Thr Leu Gln Glu Asp Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 145
<212> TYPE: PRT
<213> ORGANISM: Homo sapiens
<220> FEATURE:
<221> NAME/KEY: CARBOHYD
<222> LOCATION: (1)..(145)
```

```
-continued

<223> OTHER INFORMATION: Sites of N-glycosylation at residues 13 and 30.
      Sites of O-glycosylation at residues 121, 127, 132 and 138.
      Sites of potential nicking of internal peptide bonds after
      residues 43, 44, 45, 47 and 75.

<400> SEQUENCE: 2

Ser Lys Glu Pro Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Ser Lys Ala Pro Pro Pro Ser Leu
            115                 120                 125

Pro Ser Pro Ser Arg Leu Pro Gly Pro Ser Asp Thr Pro Ile Leu Pro
    130                 135                 140

Gln
145
```